US012733828B2

(12) United States Patent
Parthasarathy et al.

(10) Patent No.: US 12,733,828 B2
(45) Date of Patent: Sep. 15, 2026

(54) INTERFEROMETER-BASED SYNTHETIC MULTI-EXPOSURE SPECKLE IMAGING (syMESI) METHOD AND SYSTEM

(71) Applicant: UNIVERSITY OF SOUTH FLORIDA, Tampa, FL (US)

(72) Inventors: Ashwin Parthasarathy, Tampa, FL (US); Abdul Mohaimen Safi, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 18/719,461

(22) PCT Filed: Dec. 12, 2022

(86) PCT No.: PCT/US2022/052512
§ 371 (c)(1),
(2) Date: Jun. 13, 2024

(87) PCT Pub. No.: WO2023/114124
PCT Pub. Date: Jun. 22, 2023

(65) Prior Publication Data

US 2025/0049338 A1 Feb. 13, 2025

Related U.S. Application Data

(60) Provisional application No. 63/265,312, filed on Dec. 13, 2021.

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/7425* (2013.01); *G06T 7/0012* (2013.01);
(Continued)

(58) Field of Classification Search
CPC ... A61B 5/0261; A61B 5/7425; G06T 7/0012; G06T 7/20; G06T 2207/10004;
(Continued)

(56) References Cited

U.S. PATENT DOCUMENTS 7,231,243 B2 * 6/2007 Tearney ............... A61B 5/6885 600/407
8,848,199 B2 * 9/2014 Choi ...................... G01N 21/45 356/497

(Continued)

FOREIGN PATENT DOCUMENTS

WO 2020/247649 A1 12/2020

OTHER PUBLICATIONS

Xu, Jian, et al. "Interferometric speckle visibility spectroscopy (ISVS) for human cerebral blood flow monitoring." APL Photonics 5.12 (2020). 16 pages.

(Continued)

*Primary Examiner* — Dixomara Vargas
(74) *Attorney, Agent, or Firm* — Quarles & Brady LLP; Yakov S. Sidorin

(57) ABSTRACT

A SyntheticMulti-Exposure Speckle Imaging (syMESI) methodology necessarily utilizing an optical interferometer apparatus as part of the speckle imaging system to overcome the optical detector noise that conventionally limits the reliable and accurate determination of a speckle contrast characteristic at low exposure times. The use of such methodology enabled a quantitative determination of absolute value(s) of changes of motion at the target object (such as blood flow changes in tissue) at low photon budget of less than 40 counts of average detection intensity and/or quantitative imaging of the blood flow at the object in interoperative setting with a low-cost camera sensor.

8 Claims, 8 Drawing Sheets

(51) Int. Cl.
*G06T 7/00* (2017.01)
*G06T 7/20* (2017.01)

(52) U.S. Cl.
CPC ...... *G06T 7/20* (2013.01); *G06T 2207/10004* (2013.01); *G06T 2207/20048* (2013.01); *G06T 2207/20076* (2013.01); *G06T 2207/30104* (2013.01)

(58) Field of Classification Search
CPC . G06T 2207/20048; G06T 2207/20076; G06T 2207/30104
See application file for complete search history.

(56) References Cited

U.S. PATENT DOCUMENTS

| | | | | |
|---|---|---|---|---|
| 11,099,522 | B2 | 8/2021 | Atlan | |
| 2005/0094154 | A1* | 5/2005 | Baney | G06F 3/03544 356/499 |
| 2006/0024061 | A1* | 2/2006 | Wirth | H04B 10/1125 398/129 |
| 2011/0267340 | A1* | 11/2011 | Kraus | A61B 3/102 345/419 |
| 2011/0282469 | A1 | 11/2011 | Neuman | |
| 2012/0188354 | A1* | 7/2012 | Munro | H04N 23/11 348/E5.043 |
| 2015/0062590 | A1* | 3/2015 | Bagherinia | G06N 3/09 356/479 |
| 2015/0079621 | A1* | 3/2015 | An | G01N 33/689 435/29 |
| 2015/0216415 | A1* | 8/2015 | Uribe-Patarroyo | G01S 7/4808 356/450 |
| 2017/0035286 | A1* | 2/2017 | Meyer | A61B 3/1233 |
| 2018/0299251 | A1* | 10/2018 | Liba | G02B 27/48 |
| 2019/0150745 | A1* | 5/2019 | Sobek | A61B 5/0073 |
| 2019/0150751 | A1* | 5/2019 | Yang | H04N 23/45 |
| 2019/0183343 | A1* | 6/2019 | Yang | A61B 5/0035 |
| 2019/0269331 | A1* | 9/2019 | Alford | A61B 5/6803 |
| 2019/0313912 | A1* | 10/2019 | Alford | G01N 21/49 |
| 2019/0336001 | A1* | 11/2019 | Zhou | A61B 5/0066 |
| 2019/0336057 | A1* | 11/2019 | Alford | A61B 5/14553 |
| 2020/0333245 | A1* | 10/2020 | Mohseni | A61B 5/0066 |
| 2020/0386535 | A1 | 12/2020 | Brake et al. | |
| 2021/0030284 | A1 | 2/2021 | Zhou et al. | |
| 2023/0324166 | A1* | 10/2023 | Podoleanu | G02B 21/008 356/450 |
| 2024/0188840 | A1* | 6/2024 | Parthasarathy | G06T 7/0016 |

OTHER PUBLICATIONS

Han, Guang, et al. "Interferometric diffusing speckle contrast imaging (iDSCI) system for monitoring regional cerebral blood flow." Optics in Health Care and Biomedical Optics XI. vol. 11900. SPIE (2021). pp. 1190025. 13 pages.
Chammas, Marc, et al. "Synthetic exposure: a simplified and accurate acquisition scheme for multiple exposure speckle imaging of blood flow." arXiv preprint arXiv:2109.15083 (2021). 1-13.
International Search Report of Related PCT/US2022/052512, mailed Mar. 24, 2023, 4 pages.
Written Opinion of Related PCT/US2022/052512, mailed Mar. 24, 2023, 5 pages.
Zhou, Wenjun, et al. "Multi-exposure interferometric diffusing wave spectroscopy (MiDWS)." Optical Techniques in Neurosurgery, Neurophotonics, and Optogenetics. vol. 11629. International Society for Optics and Photonics, 2021.
B. Fagrell and M. Intaglietta, "Microcirculation: Its significance in clinical and molecular medicine," J. Intern. Med. (1997).
C. Ince, "The microcirculation is the motor of sepsis," Crit. Care (2005).
D. A. Boas and A. K. Dunn, "Laser speckle contrast imaging in biomedical optics," J. Biomed. Opt. 15, 011109 (2010).
J. Senarathna, S. Member, A. Rege, N. Li, and N. V Thakor, "Laser Speckle Contrast Imaging : Theory, Instrumentation and Applications," 6, 99-110 (2013).
A. B. Parthasarathy, S. M. S. Kazmi, and A. K. Dunn, "Quantitative imaging of ischemic stroke through thinned skull in mice with Multi Exposure Speckle Imaging," 1, 246-259 (2010).
C. Ayata, A. K. Dunn, Y. Gursoy-Özdemir, Z. Huang, D. A. Boas, and M. A. Moskowitz, "Laser speckle flowmetry for the study of cerebrovascular physiology in normal and ischemic mouse cortex," J. Cereb. Blood Flow Metab. (2004).
D. R. Miller, R. Ashour, C. T. Sullender, and A. K. Dunn, "Laser speckle contrast imaging for visualizing blood flow during cerebral aneurysm surgery: A comparison with indocyanine green angiography," medRxiv 2021.04.29.21254954 (2021).
A. Devor, S. Sakadić, V. J. Srinivasan, M. a Yaseen, K. Nizar, P. a Saisan, P. Tian, A. M. Dale, S. a Vinogradov, M. A. Franceschini, and D. a Boas, "Frontiers in optical imaging of cerebral blood flow and metabolism," J. Cereb. Blood Flow Metab. 32, 1259-1276 (2012).
A. Nadort, K. Kalkman, T. G. van Leeuwen, and D. J. Faber, "Quantitative blood flow velocity imaging using laser speckle flowmetry," Sci. Rep. 6, 25258 (2016).
A. Rege, K. Murari, A. Seifert, A. P. Pathak, and N. V Thakor, "Multiexposure laser speckle contrast imaging of the angiogenic microenvironment.," J. Biomed. Opt. 16, 056006 (2011).
F. Fercher and J. D. Briers, "Flow visualization by means of single-exposure speckle photography," Opt. Commun. 37, 326-330 (1981).
A. B. Parthasarathy, W. J. Tom, A. Gopal, X. Zhang, and A. K. Dunn, "Robust flow measurement with multi-exposure speckle imaging.," Opt. Express 16, 1975-1989 (2008).
Shams Kazmi, S. M., Rebecca K. Wu, and Andrew K. Dunn. "Evaluating multi-exposure speckle imaging estimates of absolute autocorrelation times." Optics letters 40.15 (2015): 3643-3646.
D. D. Postnov, J. Tang, S. E. Erdener, K. Kiliç, and D. A. Boas, "Dynamic light scattering imaging," Sci. Adv. (2020).
R. Bandyopadhyay, a. S. Gittings, S. S. Suh, P. K. Dixon, and D. J. Durian, "Speckle-visibility spectroscopy: A tool to study time-varying dynamics," Rev. Sci. Instrum. 76, 1-11 (2005).
A. M. Safi, C. Hernandez-isidro, S. Cini, S. Moka, M. Harrah, C. L. Passaglia, and A. B. Parthasarathy, "Quantitative Cerebral Blood Flow Imaging with Synthetic Single-Shot Multi-Exposure Laser Speckle Imaging," 2021, 3-4 (2021).
S. Sunil, S. Zilpelwar, D. A. Boas, and D. D. Postnov, "Guidelines for obtaining an absolute blood flow index with laser speckle contrast imaging," 2, 21-23 (2021).
M. B. Robinson, D. A. Boas, S. Sakadzic, M. A. Franceschini, and S. A. Carp, "Interferometric diffuse correlation spectroscopy improves measurements at long source-detector separation and low photon count rate," J. Biomed. Opt. (2020).
W. Zhou, O. Kholiqov, S. P. Chong, and V. J. Srinivasan, "Highly parallel, interferometric diffusing wave spectroscopy for monitoring cerebral blood flow dynamics," Optica (2018).
P. Abraham, M. Bourgeau, M. Camo, A. Humeau-Heurtier, S. Durand, P. Rousseau, and G. Mahe, "Effect of skin temperature on skin endothelial function assessment," Microvasc. Res. (2013).
G. Mahé, A. Humeau-Heurtier, S. Durand, G. Leftheriotis, and P. Abraham, "Assessment of skin microvascular function and dysfunction with laser speckle contrast imaging," Circ. Cardiovasc. Imaging (2012).
M. Hellmann, M. Roustit, F. Gaillard-Bigot, and J. L. Cracowski, "Cutaneous iontophoresis of treprostinil, a prostacyclin analog, increases microvascular blood flux in diabetic malleolus area," Eur. J. Pharmacol. (2015).
F. Iredahl, A. Löfberg, F. Sjöberg, S. Farnebo, and E. Tesselaar, "Non-invasive measurement of skin microvascular response during pharmacological and physiological provocations," PLoS One (2015).
H. Sarojini, A. Bajorek, R. Wan, J. Wang, Q. Zhang, A. T. Billeter, and S. Chien, "Enhanced Skin Incisional Wound Healing With Intracellular ATP Delivery via Macrophage Proliferation and Direct Collagen Production," Front. Pharmacol. (2021).
C. J. Stewart, C. L. Gallant-Behm, K. Forrester, J. Tulip, D. A. Hart, and R. C. Bray, "Kinetics of blood flow during healing of excisional

(56) References Cited

OTHER PUBLICATIONS full-thickness skin wounds in pigs as monitored by laser speckle perfusion imaging," Ski. Res. Technol. (2006).
J. Q. Nguyen, C. Crouzet, T. Mai, K. Riola, D. Uchitel, L.-H. Liaw, N. Bernal, A. Ponticorvo, B. Choi, and A. J. Durkin, "Spatial frequency domain imaging of burn wounds in a preclinical model of graded burn severity," J. Biomed. Opt. (2013).
A. Ponticorvo, R. Rowland, M. Baldado, D. M. Burmeister, R. J. Christy, N. P. Bernal, and A. J. Durkin, "Evaluating clinical observation versus Spatial Frequency Domain Imaging (SFDI), Laser Speckle Imaging (LSI) and thermal imaging for the assessment of burn depth," Burns (2019).
L. Tchvialeva, G. Dhadwal, H. Lui, S. Kalia, H. Zeng, D. I. McLean, and T. K. Lee, "Polarization speckle imaging as a potential technique for in vivo skin cancer detection.," J. Biomed. Opt. 18, 061211 (2013).
Y. Wang, J. Cai, D. C. Louie, H. Lui, T. K. Lee, and Z. Jane Wang, "Classifying melanoma and seborrheic keratosis automatically with polarization speckle imaging," in GlobalSIP 2019—7th IEEE Global Conference on Signal and Information Processing, Proceedings (2019).
J. Wang and S. K. Nadkarni, "The influence of optical fiber bundle parameters on the transmission of laser speckle patterns," Opt. Express (2014).
T. H. Kong, S. Yu, B. Jung, J. S. Choi, and Y. J. Seo, "Monitoring blood-flow in the mouse cochlea using an endoscopic laser speckle contrast imaging system," PLoS One (2018).
R. C. Bray, K. R. Forrester, J. Reed, C. Leonard, and J. Tulip, "Endoscopic laser speckle imaging of tissue blood flow: Application in the human knee," J. Orthop. Res. (2006).
B. Ruaro, A. Sulli, V. Smith, S. Paolino, C. Pizzorni, and M. Cutolo, "Short-term follow-up of digital ulcers by laser speckle contrast analysis in systemic sclerosis patients," Microvasc. Res. (2015).
I. Cordovil, G. Huguenin, G. Rosa, A. Bello, O. Köhler, R. de Moraes, and E. Tibiriçá, "Evaluation of systemic microvascular endothelial function using laser speckle contrast imaging," Microvasc. Res. (2012).
A. Barcelos, E. Tibirica, and C. Lamas, "Evaluation of microvascular endothelial function and capillary density in patients with infective endocarditis using laser speckle contrast imaging and video-capillaroscopy," Microvasc. Res. (2018).
J. P. Borges, A. R. Nascimento, G. O. Lopes, D. J. M. Medeiros-Lima, M. P. Coelho, P. M. C. Nascimento, D. A. Kopiler, C. Matsuura, M. F. F. Mediano, and E. Tibirica, "The impact of exercise frequency upon microvascular endothelium function and oxidative stress among patients with coronary artery disease," Clin. Physiol. Funct. Imaging (2018).
D. D. Patel and D. M. Lipinski, "Validating a low-cost laser speckle contrast imaging system as a quantitative tool for assessing retinal vascular function," Sci. Rep. (2020).
A. S. Alessandra, E. L. S. Clemente, M. de Lourdes Guimarães Rodrigues, D. C. Torres Valença, and M. B. Gomes, "Assessment of microvascular endothelial function in type 1 diabetes using laser speckle contrast imaging," J. Diabetes Complications (2017).
A. K. Dunn, H. Bolay, M. A. Moskowitz, and D. A. Boas, "Dynamic Imaging of Cerebral Blood Flow Using Laser Speckle," in Journal of Cerebral Blood Flow & Metabolism (2001), vol. 21, pp. 195-201.
T. Durduran, M. G. Burnett, G. Yu, C. Zhou, D. Furuya, A. G. Yodh, J. A. Detre, and J. H. Greenberg, "Spatiotemporal Quantification of Cerebral Blood Flow during Functional Activation in Rat Somatosensory Cortex Using Laser-Speckle Flowmetry," J. Cereb. Blood Flow Metab. (2004).
M. Li, P. Miao, Y. Zhu, and S. Tong, "Functional laser speckle imaging of cerebral blood flow under hypothermia.," J. Biomed. Opt. 16, 086011 (2011).
Y. Takeshima, H. Miyake, I. Nakagawa, Y. Motoyama, Y .- S. Park, and H. Nakase, "Visualization of Regional Cerebral Blood Flow Dynamics during Cortical Venous Occlusion using Laser Speckle Contrast Imaging in a Rat Model," J. Stroke Cerebrovasc. Dis. 24, 2200-2206 (2015).
Q. Liu, Y. Li, H. Lu, and S. Tong, "Real-time high resolution laser speckle imaging of cerebral vascular changes in a rodent photothrombosis model," Biomed. Opt. Express 5, 1483 (2014).
J. Luckl, C. Zhou, T. Durduran, A. G. Yodh, and J. H. Greenberg, "Characterization of periinfarct flow transients with laser speckle and Doppler after middle cerebral artery occlusion in the rat," J. Neurosci. Res. (2009).
N. Hecht, M. M. Müller, N. Sandow, A. Pinczolits, P. Vajkoczy, and J. Woitzik, "Infarct prediction by intraoperative laser speckle imaging in patients with malignant hemispheric stroke," J. Cereb. Blood Flow Metab. (2016).
J. Zötterman, D. Opsomer, S. Farnebo, P. Blondeel, S. Monstrey, and E. Tesselaar, "Intraoperative laser speckle contrast imaging in DIEP breast reconstruction: A prospective case series study," Plast. Reconstr. Surg.—Glob. Open (2020).
E. A. Mannoh, G. Thomas, C. C. Solórzano, and A. Mahadevan-Jansen, "Intraoperative Assessment of Parathyroid Viability using Laser Speckle Contrast Imaging," Sci. Rep. (2017).
L. M. Richards, S. S. Kazmi, K. E. Olin, J. S. Waldron, D. J. Fox, and A. K. Dunn, "Intraoperative multiexposure speckle imaging of cerebral blood flow," J. Cereb. Blood Flow Metab. 0271678X1668698 (2017).
S. Kojima, T. Sakamoto, Y. Nagai, Y. Matsui, K. Nambu, and K. Masamune, "Laser Speckle Contrast Imaging for Intraoperative Quantitative Assessment of Intestinal Blood Perfusion During Colorectal Surgery: A Prospective Pilot Study," Surg. Innov. (2019).
S. Nomura, T. Inoue, H. Ishihara, H. Koizumi, E. Suehiro, F. Oka, and M. Suzuki, "Reliability of laser speckle flow imaging for intraoperative monitoring of cerebral blood flow during cerebrovascular surgery: Comparison with cerebral blood flow measurement by single photon emission computed tomography," World Neurosurg. (2014).
R. Ambrus, L. B. Svendsen, N. H. Secher, K. Rünitz, H. J. Frederiksen, M. B. S. Svendsen, M. Siemsen, S. C. Kofoed, and M. P. Achiam, "A reduced gastric corpus microvascular blood flow during Ivor-Lewis esophagectomy detected by laser speckle contrast imaging technique," Scand. J. Gastroenterol. (2017).
N. Hecht, M. Schrammel, K. Neumann, M. M. Müller, J. P. Dreier, P. Vajkoczy, and J. Woitzik, "Perfusion-Dependent Cerebral Autoregulation Impairment in Hemispheric Stroke," Ann. Neurol. (2021).
J. Woitzik, N. Hecht, A. Pinczolits, N. Sandow, S. Major, M. K. L. Winkler, S. Weber-Carstens, C. Dohmen, R. Graf, A. J. Strong, J. P. Dreier, and P. Vajkoczy, "Propagation of cortical spreading depolarization in the human cortex after malignant stroke," Neurology (2013).
A. Mangraviti, F. Volpin, J. Cha, S. I. Cunningham, K. Raje, M. J. Brooke, H. Brem, A. Olivi, J. Huang, B. M. Tyler, and A. Rege, "Intraoperative Laser Speckle Contrast Imaging for Real-Time Visualization of Cerebral Blood Flow in Cerebrovascular Surgery: Results From Pre-Clinical Studies," Sci. Rep. (2020).
L. M. Richards, E. L. Towle, D. J. Fox, and A. K. Dunn, "Intraoperative laser speckle contrast imaging with retrospective motion correction for quantitative assessment of cerebral blood flow," Neurophotonics (2014).
C. To, J. E. Rees-Lee, R. J. Gush, K. M. Gooding, N. H. Cawrse, A. C. Shore, and A. D. H. Wilson, "Intraoperative Tissue Perfusion Measurement by Laser Speckle Imaging: A Potential Aid for Reducing Postoperative Complications in Free Flap Breast Reconstruction," Plast. Reconstr. Surg. (2019).
E. A. Mannoh, G. Thomas, N. Baregamian, S. L. Rohde, C. C. Solórzano, and A. Mahadevan-Jansen, "Assessing Intraoperative Laser Speckle Contrast Imaging of Parathyroid Glands in Relation to Total Thyroidectomy Patient Outcomes," Thyroid (2021).
S. Eriksson, J. Nilsson, G. Lindell, and C. Sturesson, "Laser speckle contrast imaging for intraoperative assessment of liver microcirculation: A clinical pilot study," Med. Devices Evid. Res. (2014).
N. Hecht, J. Woitzik, S. Konig, P. Horn, and P. Vajkoczy, "Laser speckle imaging allows real-time intraoperative blood flow assessment during neurosurgical procedures," J. Cereb. Blood Flow Metab. (2013).
A. Bonaroti, R. C. Decoster, S. Mazdeyasna, C. Huang, G. Yu, F. J. Halcomb, and L. Wong, "The Role of Intraoperative Laser Speckle Imaging in Reducing Postoperative Complications in Breast Reconstruction," Plast. Reconstr. Surg. (2019).

(56) References Cited

OTHER PUBLICATIONS

G. Dietsche, M. Ninck, C. Ortolf, J. Li, F. Jaillon, and T. Gisler, "Fiber-based multispeckle detection for time-resolved diffusing-wave spectroscopy: Characterization and application to blood flow detection in deep tissue," Appl. Opt. (2007).
K. Murali, A. K. Nandakumaran, T. Durduran, and H. M. Varma, "Recovery of the diffuse correlation spectroscopy data-type from speckle contrast measurements: towards low-cost, deep-tissue blood flow measurements," Biomed. Opt. Express (2019).
J. Liu, H. Zhang, J. Lu, X. Ni, and Z. Shen, "Quantitative model of diffuse speckle contrast analysis for flow measurement," J. Biomed. Opt. (2017).
R. Bi, J. Dong, and K. Lee, "Deep tissue flowmetry based on diffuse speckle contrast analysis," Opt. Lett. (2013).
C. Huang, M. Seong, J. P. Morgan, S. Mazdeyasna, J. G. Kim, J. T. Hastings, and G. Yu, "Low-cost compact diffuse speckle contrast flowmeter using small laser diode and bare charge-coupleddevice," J. Biomed. Opt. (2016).
R. Bi, J. Dong, and K. Lee, "Multi-channel deep tissue flowmetry based on temporal diffuse speckle contrast analysis," Opt. Express (2013).
C. Huang, S. Mazdeyasna, L. Chen, E. G. Abu Jawdeh, H. S. Bada, K. E. Saatman, L. Chen, and G. Yu, "Noninvasive noncontact speckle contrast diffuse correlation tomography of cerebral blood flow in rats," Neuroimage (2019).
C. Huang, D. Irwin, Y. Lin, Y. Shang, L. He, W. Kong, J. Luo, and G. Yu, "Speckle contrast diffuse correlation tomography of complex turbid medium flow," Med. Phys. 42, 4000-4006 (2015).
R. Bi, Y. Du, G. Singh, J .- H. Ho, S. Zhang, A. B. Ebrahim Attia, X. Li, and M. C. Olivo, "Fast pulsatile blood flow measurement in deep tissue through a multimode detection fiber," J. Biomed. Opt. (2020).
C. P. Valdes, H. M. Varma, A. K. Kristoffersen, T. Dragojevic, J. P. Culver, and T. Durduran, "Speckle contrast optical spectroscopy, a non-invasive, diffuse optical method for measuring microvascular blood flow in tissue," Biomed. Opt. Express 5, 2769 (2014).
Z. Hajjarian and S. K. Nadkarni, "Evaluation and Correction for Optical Scattering Variations in Laser Speckle Rheology of Biological Fluids," PLoS One (2013).
Z. Hajjarian, H. T. Nia, S. Ahn, A. J. Grodzinsky, R. K. Jain, and S. K. Nadkarni, "Laser Speckle Rheology for evaluating the viscoelastic properties of hydrogel scaffolds," Sci. Rep. (2016).
Z. Hajjarian and S. K. Nadkarni, "Correction of optical absorption and scattering variations in Laser Speckle Rheology measurements.," Opt. Express 22, 6349-61 (2014).
Z. Hajjarian and S. K. Nadkarni, "Estimation of particle size variations for laser speckle rheology of materials," Opt. Lett. (2015).
J. Ruiz-López, A. B. Rodríguez-Aguila, A. Yebra, A. M. Pozo, J. D. Tarifa-Bonilla, and M. d. Pérez Gómez, "Laser speckle rheology for evaluating mechanical properties of biomaterials: a pilot study," in (2019).
Z. Hajjarian, E. Brachtel, D. Tshikudi, and S. Nadkarni, "Laser Speckle Micro-rheology for biomechanical mapping of breast carcinoma," in Optics InfoBase Conference Papers (2020).
Z. Hajjarian and S. K. Nadkarni, "Evaluating the Viscoelastic Properties of Tissue from Laser Speckle Fluctuations," Sci. Rep. 2, (2012).
S. K. Nadkarni, "Optical measurement of arterial mechanical properties: from atherosclerotic plaque initiation to rupture," J. Biomed. Opt. (2013).
Z. Hajjarian, M. M. Tripathi, and S. K. Nadkarni, "Optical Thromboelastography to evaluate whole blood coagulation," J. Biophotonics (2015).
Z. Hajjarian, D. M. Tshikudi, and S. K. Nadkarni, "Evaluating platelet aggregation dynamics from laser speckle fluctuations," Biomed. Opt. Express (2017).
H. J. Jeon, M. M. Qureshi, S. Y. Lee, J. D. Badadhe, H. Cho, and E. Chung, "Laser speckle decorrelation time-based platelet function testing in microfluidic system," Sci. Rep. (2019).
M. M. Tripathi, Z. Hajjarian, E. M. Van Cott, and S. K. Nadkarni, "Assessing blood coagulation status with laser speckle rheology," Biomed. Opt. Express (2014).
Y. D. Liushnevskaya, F. A. Gubarev, L. Li, A. V. Nosarev, and V. S. Gusakova, "Measurement of Whole Blood Coagulation Time by Laser Speckle Pattern Correlation," Biomed. Eng. (NY). (2020).
L. Li, I. D. Sytnik, F. A. Gubarev, and Y. S. Pekker, "Evaluation of Blood Plasma Coagulability by Laser Speckle Correlation," Biomed. Eng. (NY). (2018).
Y. Piederrière, J. Cariou, Y. Guern, G. Le Brun, B. Le Jeune, J. Lotrian, J. F. Abgrall, and M. T. Blouch, "Evaluation of blood plasma coagulation dynamics by speckle analysis," J. Biomed. Opt. (2004).
M. Faivre, P. Peltié, A. Planat-Chrétien, M.-L. Cosnier, M. Cubizolles, C. Nougier, C. Négrier, and P. Pouteau, "Coagulation dynamics of a blood sample by multiple scattering analysis," J. Biomed. Opt. (2011).
First Examination Report, Indian Application No. 202427052723 dated Apr. 22, 2026.

* cited by examiner

High Contrast (low flow)
'Raw' Speckle Image
(A)
Low Contrast (high flow)
Window
$K = \frac{\sigma}{\langle I \rangle}$
(B)
Speckle Contrast Image
(C)
CCD Camera
To Computer
130
110
Diode laser
To diode controller
Zoom lens
128
Collimation optics
124
104
100
Sample 120

FIG. 7A ACQUIRED WITH EMBODIMENT 100; SINGLE EXPOSURE
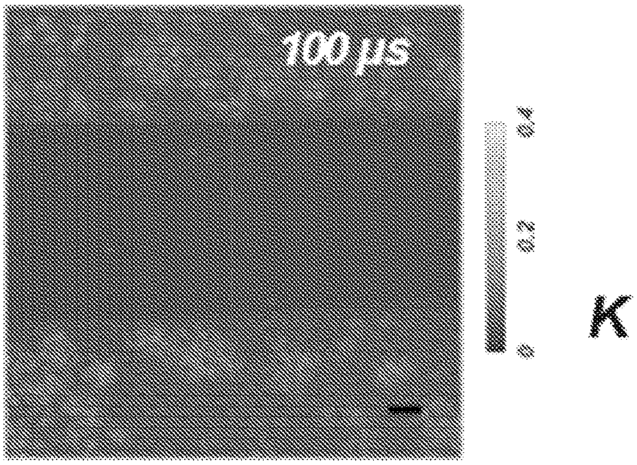
FIG. 7B ACQUIRED WITH EMBODIMENT 400; SYNTHETIC MULTI- EXPOSURE
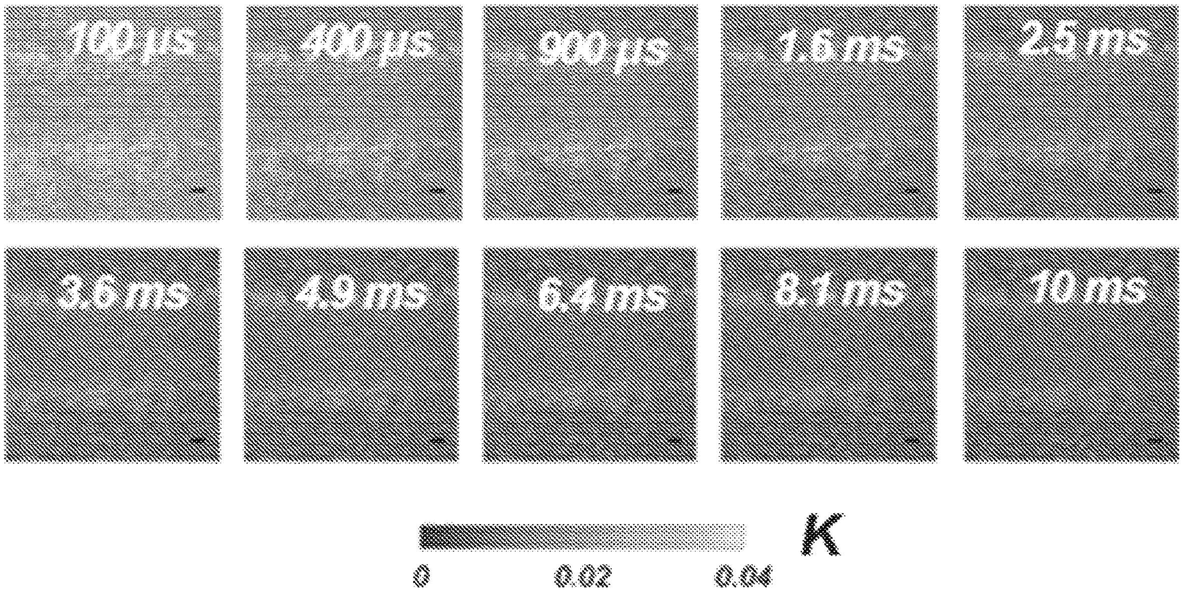

Speckle Variance, $K^2$ (a.u.)

$\times 10^{-4}$

Exposure Times (s)

1 mm/s 7 mm/s

Baseline $\tau_c/\tau_c$

Relative change in speed

810

820

INTERFEROMETER-BASED SYNTHETIC MULTI-EXPOSURE SPECKLE IMAGING (syMESI) METHOD AND SYSTEM

CROSS-REFERENCE TO RELATED APPLICATIONS

This US Patent Application is a national phase of the International Application PCT/US2022/052512 filed on Dec. 12, 2022 and now published as WO 2023/114124 which in turn claims priority from and benefit of the U.S. Provisional Patent Application No. 63/265,312 filed on Dec. 13, 2021. The disclosure of each of the above-identified patent documents is incorporated herein by reference.

RELATED ART

Blood flow through tissue serves as an important physiological index of health of such tissue, because blood flow directly indicates oxygen delivery to the tissue and is critical for normal tissue functioning. Since even small changes in oxygen supply to the brain, for example, can have a dramatic impact on normal physiological processes, reduction in blood flow to the brain is not without serious consequences. Therefore, imaging of blood flow is important to understand the normal functioning of physiology, monitor disease progression, and to track treatment.

Generally, superior spatiotemporal resolution characteristics of optical imaging methods make them more suitable for visualizing cerebral blood flow (CBF) dynamics than, for example, Magnetic Resonance Imaging (MRI), Computed Tomography (CT), or Diffuse Optical Tomography (DOT)—especially for applications that require resolution of individual cerebral blood vessels. Optical imaging methodologies rooted in photon correlation, for example (such as Laser Speckle Contrast Imaging, or LSCI) are particularly well suited for assessing the CBF with the use of intrinsically contrast motion of red blood cells.

LSCI, in particular, has been shown useful for imaging cerebral blood flow in small animal models. One of primary advantages of LSCI is its ability to obtain wide-field CBF images with superior spatial and temporal resolution while the employed imaging apparatus is simple and inexpensive. To date, LSCI has been utilized to image CBF dynamics during ischemia in rat and mouse brains, in functional activation studies, and to model ischemic stroke progression.

As is recognized in related art, laser speckle is the random interference pattern produced by coherent addition of light fields (for example, of laser light fields) that have backscattered from a sample along trajectories with slightly different path lengths. To this end, FIG. 1C schematically shows a typical LSCI setup. Here, slightly divergent light 104 from a visible or near infrared diode laser light source 110 is directed to impinge on the tissue sample 120; light 104 scatters in the tissue while the optical field components travelling along different paths through the tissue 120 experience different phase shifts. The backscattered by light 124—is collected through an imaging lens 128 and recorded, in the form of a speckle image, on the camera sensor 130 for data processing at the appropriately configured electronic circuitry 130.

The movements of particles (such as, for example, red blood cells) in the sample, cells, impress spatial and temporal fluctuations onto the speckle pattern. Such effect manifests as local blurring (or decorrelation) in the image (FIG. 1A). Quantification of this blurring or decorrelation provides a measure of flow of red blood cells in the vasculature of the tissue 120. Formally, the local speckle contrast, $K=\sigma s/\langle I\rangle$, i.e., the square root of normalized variance of local intensity, is computed in a small window (usually 7×7 pixels) within the image; here, $\sigma_s$ is the standard deviation of the intensities in the 7×7 pixel window, and $\langle I\rangle$ is the mean of intensities in the 7×7 pixel window. The processed speckle contrast image (FIG. 1B) is then produced by repeating this computation, window-by-window, across the raw speckle image. The higher value of speckle contrast in a given portion of the image of FIG. 1B is a manifestation of the reduced amount of spatial blurring in the corresponding region of the sample (i.e., in FIG. 1A), which is a direct consequence of slow-moving red blood cells.

Notably, as recognized in related art, speckle contrast measured with the LSCI approach is appropriate only for acute measurements of relative changes of the CBF changes. In other words, the results of practical use of the conventional implementation of the LSCI system does not allow for quantitative measurement of movement at or in the target tissue, producing instead assessment of the relative (for example, on the scale of arbitrary units from 0 to 1) contrast values across the speckle image that manifests only in and affords only one resulting conclusion about the CBF changes, which can be expressed as follows: a movement of the target particles (say, blood flow) at the first region of the target tissue depicted in the first portion of the image is occurring quicker than a movement of the target particles at the second region of the target tissue depicted in the second portion of the image. The quantitative (that is, numerical) assessment of the speed values of these two movements are simply not possible based on the conventional LSCI, which provides relative—that is, comparative—results. As a result, the application of the conventional LSCI system has been limited to only the very simplest of situations.

The methodology known as Multi-Exposure Speckle Imaging (or, MESI) was introduced to correct the inability of the conventional LSCI to provide quantitative measurements of blood flow by processing laser speckle images acquired at multiple camera exposures and fitting them to a quantitative speckle visibility model. To-date, MESI has been accomplished by either time-gating the laser using relatively bulky and slow instrumentation such as an acousto-optic modulator or a rotating filter wheel (see, e.g., Parthasarathy et al., "Robust flow measurement with multi-exposure speckle imaging," Optics Express 16, 1975-1989; 2008) or using temporal binning approach (albeit with an expensive fast detector better suited for low-resolution images, such as 8×5 pixels, only; see, e.g., Dragojević et al., "High-speed multi-exposure laser speckle contrast imaging with a single-photon counting camera," Biomedical Optics Express 6, 2865-2876; 2015). The well-recognized shortcomings of the MESI approach manifests in the need to use of dedicated piece of hardware taking care of maintaining the useful laser output power constant at the sample (tissue) being interrogated and/or duration of the measurements that is not short enough for multiple practical applications.

Recently, a software based synthetic MESI (syMESI) methodology was proposed (see, for example, PCT/US2022/022734 published as WO 2022/212636, the disclosure of which is incorporated herein by reference; or see Safi, Abdul Mohaimen, et al. "Quantitative Cerebral Blood Flow Imaging with Synthetic Single-Shot Multi-Exposure Laser Speckle Imaging." *Optics and the Brain.* Optical Society of America, 2021). This methodology, which just like the traditional MESI approach utilizes the collection of only (a single beam of) light scattered by/from the target scene or sample, equipped the user with the ability to perform quantitative blood flow imaging (that is, the one as a result of which an absolute, actual value (and not the value determined relatively with respect to some reference value) of an index of motion associated with a portion of the scene of interest over even entire scene of interest can be determined) without hardware typically required for implementation of MESI. However, each of the traditional hardware-based multi-exposure speckle imaging (MESI) and the recently-developed software-based synthetic multi-exposure (syMESI) approaches requires the acquisition of speckle images at very short exposure times (on the order of 50 μs or so). At such short exposure time, as the skilled artisan will readily appreciate, noise associated with the operation of the optical detector that is used for the imaging process can and often does overwhelm the useful signal (the one produced by the light backscattered from the sample and collected by the system), under which conditions the use of high-illumination optical power for imaging becomes a necessity. Such an inevitable requirement, however, may not be suitable for clinical settings such as intraoperative imaging and ophthalmology.

The current state of the art begs a question of how to avoid the use of high-power sources of light (which would otherwise be impractical for use in desired applications) while at the same time, preserving the technical and/or operational advantages already demonstrated by related art.

SUMMARY OF THE INVENTION

Embodiments of the invention provide a speckle imaging system that is configured to detect a motion, which imaging system includes an optical illumination system containing a source of light and configured to produce a light output at an output end thereof, and an optical interferometer apparatus having a reference arm and a sample arm and optically coupled with the output end of the optical illumination system. (Such optical interferometer apparatus is structured to not require and/or to not allow for a change of optical phase difference between a sample light propagating through the sample arm and a reference light propagating through the reference arm.) The speckle imaging system additionally incorporates an optical imaging system that contains an optical detector system optically cooperated with the output end, as well as a computer system (operably connected with the optical imaging system and configured to receive from it an electrical signal that represents a raw speckle image formed at the optical detector system in light output from the optical interferometer apparatus). The light output includes both the sample light (that has interacted with a target sample in the sample arm and that contains a speckle pattern representing the target sample) and the reference light. Furthermore, the speckle imaging system includes a computer-readable tangible non-transitory medium comprising a computer-readable program code on which are stored computer-readable instructions such that—when the instructions are executed by a processor of the computer system—the instructions cause the processor at least to determine and/or display a speckle contrast characteristic of said raw speckle image. In at least one implementation, the instructions are configured further cause the processor (a) to display said speckle image as a visually perceivable spatial distribution of optical irradiance; and/or (b) to determine and/or display a speckle visibility curve of values of the speckle contrast characteristic of the speckle image as a function of the target sample exposure times; and/or (c) to determine and/or display a multiplicity of speckle contrast images and/or the speckle visibility curve as a map showing a spatial distribution and/or a temporal distribution of changes of said motion at the target sample.

Substantially in every implementation, the speckle imaging system may be configured to satisfy at least one of the following conditions: 1) to have a dynamic range of measurement of the speckle contrast characteristic to necessarily depend on intensity of the reference light; and/or 2) to include at least one device configured to control an intensity of the sample light and/or an intensity of the reference light; and/or 3) to incorporate the instructions that cause the processor to ascertain the speckle variance of the raw speckle image while maintaining such variance to be larger than a variance of noise of the optical detector; and/or 4) to incorporate the instructions that cause the processor to ascertain the speckle variance of said raw speckle image while maintaining such speckle variance to be larger than a variance of noise of the optical detector substantially regardless of a level of non-zero intensity of the first portion of said light; and/or 5) to incorporate the instructions that cause the processor to quantitatively determine an absolute value of an index of motion over a portion of the scene or over the entire scene represented by a given pixel of the raw speckle image; and/or 6) to incorporate the instructions that cause the processor (i) to calculate a value of speckle contrast of the raw speckle image for each identified pixel or group of pixels of the optical detector as a first ratio of a normalized value of a standard deviation of intensities of light at pixels within a chosen area of the optical detector surrounding such identified pixel to a mean value of said intensities, or as a second ratio of a normalized value of a standard deviation of intensities of light at the identified pixel to a mean value of such intensities of light at the identified pixel calculated over multiple exposure times, and/or (ii) to determine the first ratio and/or the second ratio in a temporal domain, a spatial domain, or a spatio-temporal domain.

In at least one of the above-identified embodiments, the speckle imaging system may be configured as a multiple-synthetic exposure-time speckle imaging (syMESI) system, in which the optical illumination system does not include an apparatus that is structured to maintain a power of said light output to be substantially constant over exposure time, and/or such syMESI system may contain the instructions that cause the processor (i) to acquire, at only one fixed first empirical exposure time, one or more raw speckle images formed in said light by the imaging system; and (ii) to spatially average a chosen raw speckle image of the one or more raw speckle images with use of multiple binning apertures that have spatial different dimensions to form respectively-corresponding modified speckle images, where each of such modified speckle images represents a speckle image corresponding to a respectively-corresponding second synthetic exposure time from a plurality of second synthetic exposure times (and where each second synthetic exposure time from the plurality of second synthetic exposure times is different from one another and from the first empirical exposure time). In the latter case, the instructions may be additionally configured to cause the processor to transform each of the modified speckle images into a respectively-corresponding speckle contrast image of a plurality of speckle contrast images and/or speckle visibility curves corresponding to the same chosen image. Alternatively or in addition, the instruction may be configured to cause the processor to assess, based at least on the speckle visibility curve, a quantitative value of a motion at a portion of a scene irradiated with the light output in operation of the speckle imaging system and represented by the one or more raw speckle images. Alternatively or in addition, the instructions may be configured to cause the processor to generate a visually perceivable image of a portion of a scene irradiated with the light output in operation of the speckle imaging system and represented by the one or more raw speckle images (here, the visually perceivable image displays a spatial distribution of a quantitative value of a motion at said portion of the scene via a spatial distribution of an optical parameter across said visually perceivable image). Alternatively or in addition, the instructions may be configured to cause the processor to acquire, at only such one fixed first empirical exposure time, a sequence of raw speckle images by the imaging system (such that constituent raw speckle images in the sequence are necessarily non-consecutive). In the latter case, the optical imaging system may be configured to acquire such necessarily non-consecutive raw speckle images with time gaps of different durations in-between immediately neighboring raw speckle images.

Embodiments of the invention additionally provide a method for characterizing a scene with a speckle imaging system (which, in at least one case, can be configured according to any one embodiment identified above). Such method includes the steps of a) coupling light generated by a light source of the speckle imaging system into an optical interferometer apparatus of the speckle imaging system (here, the speckle imaging system is configured to detect motion and the optical interferometer apparatus does not require and/or does not allow for a change of optical phase difference between a sample arm and a reference arm thereof); b) irradiating the scene with a first portion (of light generated by the light source) that propagates through the sample arm of the optical interferometer apparatus; c) spatially overlapping, at an optical detector of the optical detection system of the speckle imaging system, a second portion (of such light, that has propagated through the reference arm of the optical interferometer apparatus) with the first portion of light that has interacted with the scene to thereby form an output light that contains both the first portion backscattered by the scene and the second portion. Additionally, the method includes a step of acquiring, at a given exposure time, a raw speckle image of the scene in the output light with an optical detector.

In at least one implementation (and when the operational parameter of the optical interferometer apparatus does not include intensity of the second portion of light generated by the light source), the method is configured to be devoid of changing such operational parameter of the optical interferometer apparatus during the steps of coupling, irradiating, overlapping. In at least one specific case of such implementation, the method may additionally include a step of varying a dynamic range of a speckle contrast characteristic of the raw speckle image by modifying the intensity of the second portion of light.

Alternatively or in addition—and substantially in every implementation of the method—the method may include determining a speckle contrast characteristic of the raw speckle image as a function of a ratio of intensity of the second portion of light to intensity of the output light (where such ratio is optionally time-dependent) and/or additionally include varying a dynamic range of the speckle contrast characteristic of the raw speckle image by modifying the intensity of at least one of the first portion of light and the second portion of light.

Alternatively or in addition—and substantially in every implementation—the method may be configured to include ascertaining a speckle variance of the raw speckle image while maintaining such speckle variance to be larger than a variance of noise of the optical detector. (Here, such maintaining optionally includes maintaining the speckle variance to be larger than the variance of noise of the optical detector substantially regardless of a level of non-zero intensity of the first portion of light generated by the light source.

Alternatively or in addition—and substantially in every implementation—the method may be configured to satisfy at least one of the following conditions: (a) to additionally include a step of quantitatively determining an absolute value of an index of motion at a portion of the scene represented by a given pixel of the raw speckle image; and (b) to have such index of motion to be an index of blood flow when the scene is a biological tissue.

Alternatively or in addition, and substantially in every implementation, the method may include (1) a step of calculating a value of speckle contrast of the raw image for each identified pixel of the optical detector either as a first ratio of a normalized value of a standard deviation of intensities of light at pixels within a chosen area of the optical detector surrounding such identified pixel to a mean value of said intensities, or as a second ratio of a normalized value of a standard deviation of intensities of light at the identified pixel to a mean value of such intensities of light at the identified pixel taken over multiple exposure times, and/or (2) a step of calculating the first ratio and/or the second ratio in a temporal domain, a spatial domain, or a spatio-temporal domain.

Alternatively or in addition, and substantially in every implementation, the step of acquiring may include acquiring, at only one fixed first empirical exposure time, one or more raw speckle images of the scene in the output light while the method additionally includes—for each of a plurality of binning apertures that have different spatial dimensions—a step of modifying a chosen image of the one or more raw speckle images into a corresponding one of multiple modified speckle images by spatially averaging an irradiance distribution of said chosen image with a respectively-corresponding binning aperture of the plurality of binning apertures, thereby producing a plurality of modified speckle images each of which represents a speckle image of the scene corresponding to a second synthetic exposure time of a plurality of second synthetic exposure times (here, all second synthetic exposure times from the plurality of second exposure times are different from one another and from the first empirical exposure time). In the specific version of the latter, the method may transform each of the plurality of modified speckle images into a respectively-corresponding speckle contrast image of a plurality of speckle contrast images corresponding to the same chosen image; and/or utilize the source of light that is a laser source of light; and/or ensure that—for each of modified speckle image from the plurality of modified speckle images—a numerical relationship between the first empirical exposure time and the corresponding second synthetic exposure time depends on a dimension of the pre-determined binning aperture; and/or to provide at least one of the one or more of raw speckle images, the chosen image, and at least one of the plurality of speckle contrast images that is visually perceivable. Optionally, the at least one or more raw speckle images includes only one raw speckle image; or two raw speckle images of such one of more raw speckle images that are acquired consecutively are acquired not immediately one after another but with an arbitrary time delay between such two images. In at least one implementation, the method satisfies one or more of the following two conditions: (i) the step of acquiring (at only one fixed first exposure time, of one or more raw speckle images) includes acquiring only one raw speckle image; and (ii) the step modifying a chosen image of the one or more initial speckle images includes modifying of only one image of the one or more raw speckle images. At least one implementation, at least one of the following conditions is satisfied: (1) the method quantitatively determining an absolute value of an index of motion at a portion of the scene represented by a given pixel of the chosen image; and (2) such index of motion is an index of blood flow when said scene is a biological tissue.

Alternatively or in addition—and at least in one embodiment—the step of acquiring may include acquiring multiple raw speckle images with time-gaps in-between at only one fixed first empirical exposure time to form a sequence of raw speckle images in which constituent raw speckle images are necessarily non-consecutive. In at least one case, the step of acquiring may include acquiring such necessarily non-consecutive raw speckle images with time gaps of different durations in between different immediately neighboring raw speckle images.

BRIEF DESCRIPTION OF THE DRAWINGS

For a more complete understanding of the disclosure, reference is made to the following detailed description and accompanying Drawings, of which:

FIG. 1A presents a 'raw' speckle image acquired by camera. The raw image displays random interference pattern. FIG. 1B is a processed (on the basis of the image of FIG. 1A) 'speckle contrast' image that highlights spatial regions of high and low blood flow. FIG. 1C schematically illustrates a typical LSCI apparatus configured for two-dimensional imaging of cerebral blood flow.

FIGS. 7A, 7B illustrate the comparison between the speckle contrast maps obtained with speckle imaging performed with the use of conventional embodiment 300 of the speckle imaging system of FIG. 3 (single exposure) and those performed with the embodiment of the invention (400, of FIG. 4; synthetic multi-exposure) for flow rate 5 mm/s, Scale bar: 50 μm.

DETAILED DESCRIPTION OF THE INVENTION

As was alluded to above, the currently-used in related art speckle imaging technique referred to as Multi-Exposure Speckle Imaging (or MESI) and that referred to as synthetic MESI (or, syMESI) combine a more complex (as compared to that of the conventional LSCI system) instrument design with new but different mathematical models for conversion of speckle contrast into quantitative indices of blood flow.

Traditional LSCI methodology, according to which the speckle produced by backscattering of light is imaged with a single fixed exposure duration, is suitable for measuring of relative flow changes. As a result, the applicability of traditional LSCI is limited to very simplest of situations. In conventional LSCI, speckle contrast depends on the camera exposure duration, i.e., camera exposure duration modulates the 'visibility' of blood vessels of different flow rates. Short exposure time allows to detect fast rate motion or flow, while longer exposure durations are needed to detect slow speckle intensity fluctuations associated with slow motion/flow.

Figure 2:
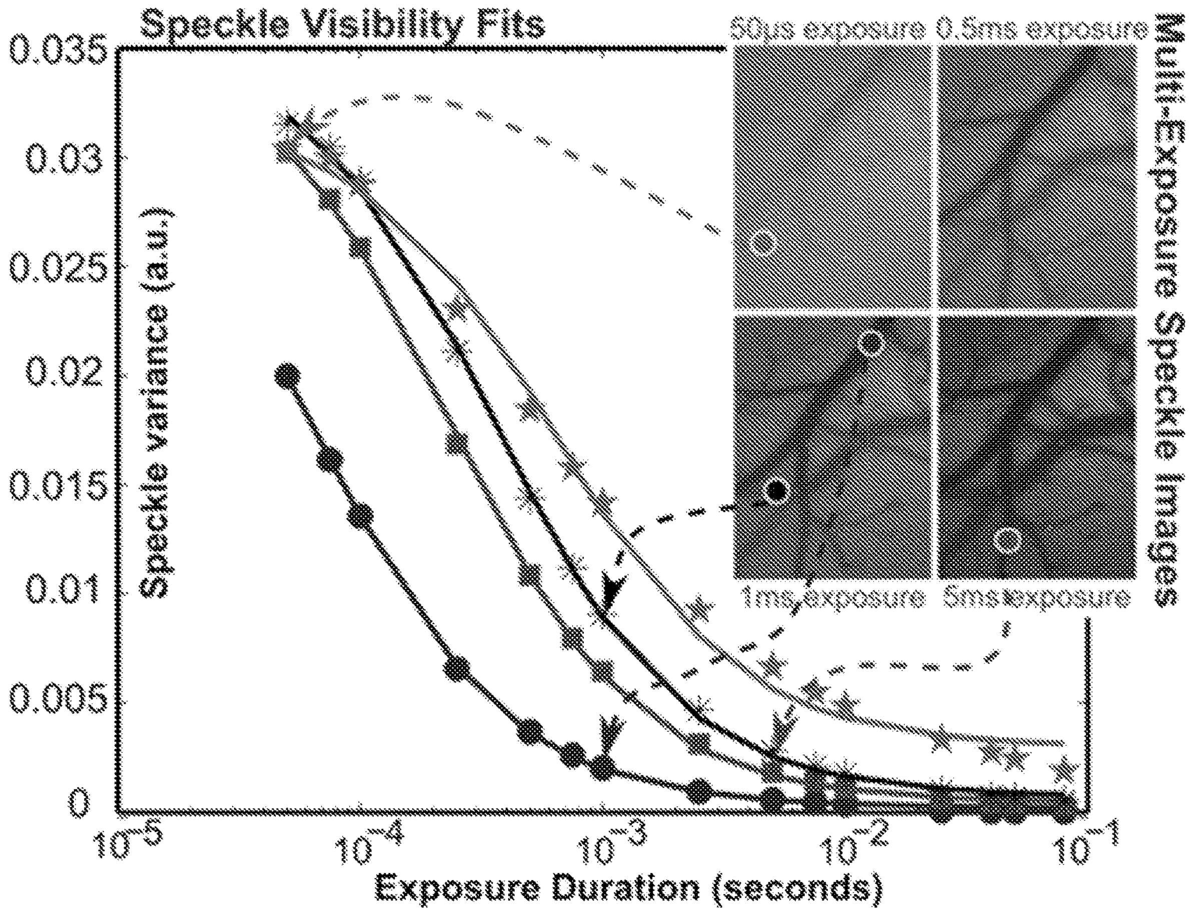
FIG. 2 illustrates the results of Multi-Exposure Speckle Imaging (MESI) of rat brain. Speckle variance as a function of camera exposure duration, T, is fit to the speckle visibility equation to derive quantitative estimates of CBF at four regions of interest. Images in inset are speckle contrast images of CBF in a mouse cortex. Camera exposure duration modulates the visibility of blood vessels.

Hardware-based MESI leverages this phenomenon and is experimentally suitable for recording speckle images at camera exposures of different durations (50 μs to 80 ms, as shown in FIG. 2). Practically, this is accomplished by externally triggering the camera acquisition and laser, while ensuring that illumination power is kept relatively constant across the dynamic range of the measurement.

Figure 3:
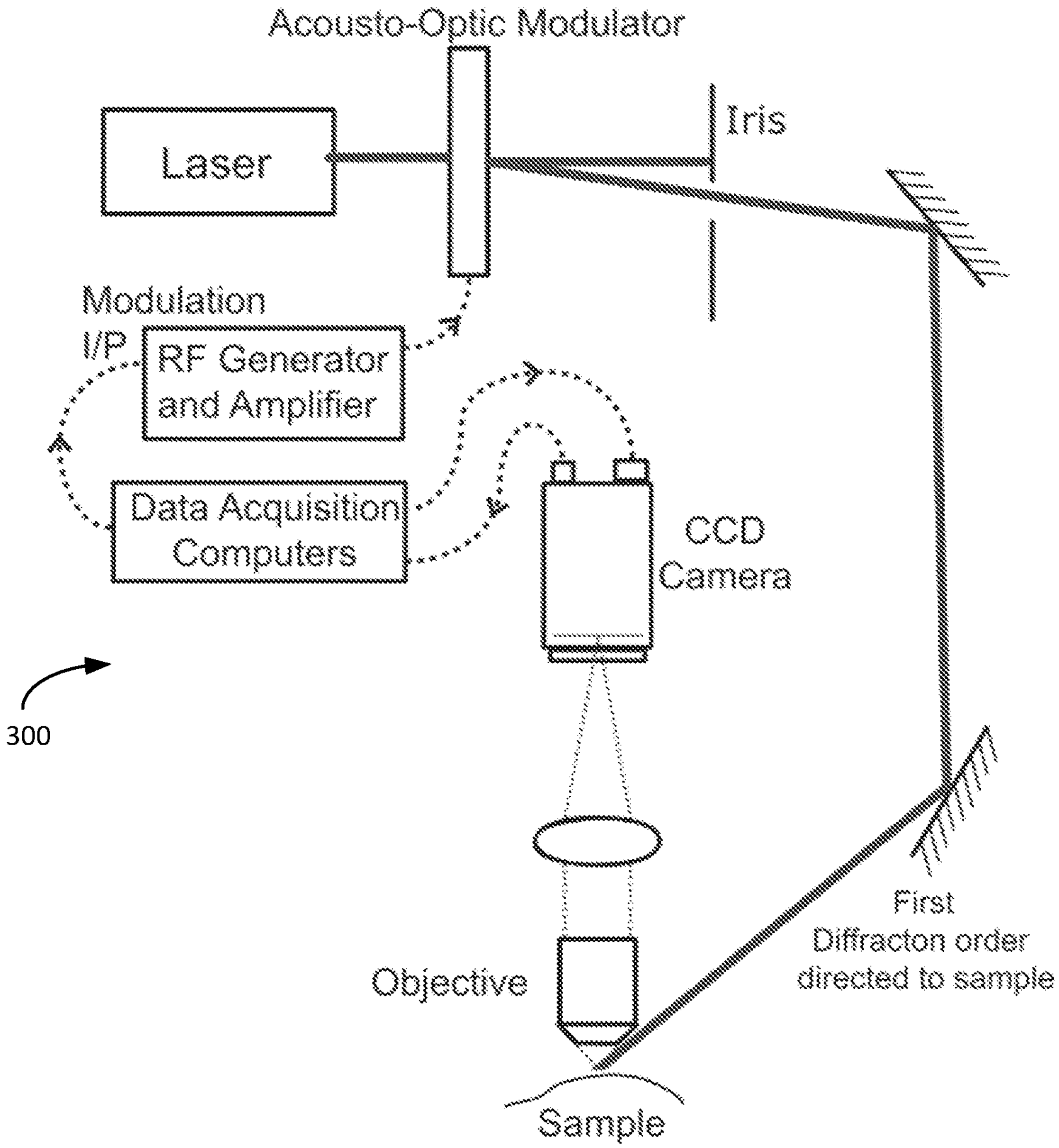
FIG. 3 schematically illustrates a typical setup for Multi-Exposure Speckle Imaging (MESI). An Acousto-Optic Modulator (AOM) is required to modulate the intensity of the laser over different exposure times. The camera and AOM are typically triggered with the data acquisition electronic circuitry (processor).

In practice, such leveraging is accomplished by externally triggering the camera acquisition and the laser light source while ensuring that power level of irradiation of the sample is kept substantially constant across the dynamic range of the measurement (see for example Parthasarathy, A. B., et al., *Optics Express* 16, 1975-1989; 2008)). The relationship between speckle contrast and camera exposure duration can be characterized by a speckle visibility equation which in its simplest form is given by: $K(T, \tau_c)=\beta(e^{-2x}-1+2x)/2x^2$. Here, $x=T/\tau_c$, $\beta$ is a speckle instrumentation factor that depends on wavelength of light, detector pixel size and speckle size, T is the camera exposure duration and Tc is the speckle decorrelation time—a quantitative index that is inversely proportional to blood flow. $\beta$ and $\tau_c$ are estimated from a nonlinear curve fit (see FIG. 2) of the multi-exposure-time speckle data (that is, speckle data acquired by the optical detector at multiple exposure times independently) to the speckle visibility expression. This multi-exposure-time MESI methodology was shown to enable the determination of $\beta$, which acts as an instrument and sample dependent calibration factor, thereby permitting imaging of baseline/absolute blood flow. In situ measurements of $\beta$ can also be used to quantitatively estimate blood flow index ($\tau_c$) from single exposure LSCI measurements. MESI was demonstrated to correct underestimation of large CBF changes and with a robust speckle visibility expression, reduced the sensitivity of speckle imagers to static tissue elements such as the skull. However, due to the bulky, complex and low temporal resolution limits the application of traditional hardware based MESI. FIG. 3 shows a typical implementation 300 of the MESI measurement apparatus used for speckle imaging, where an acousto-optic modulator (AOM) is used to control the intensity of the laser light source used for speckle imaging. (Alternatively, an array of neutral density filters can be used to control the optical power of the illumination.)

Figures 1A, 1B, 1C:
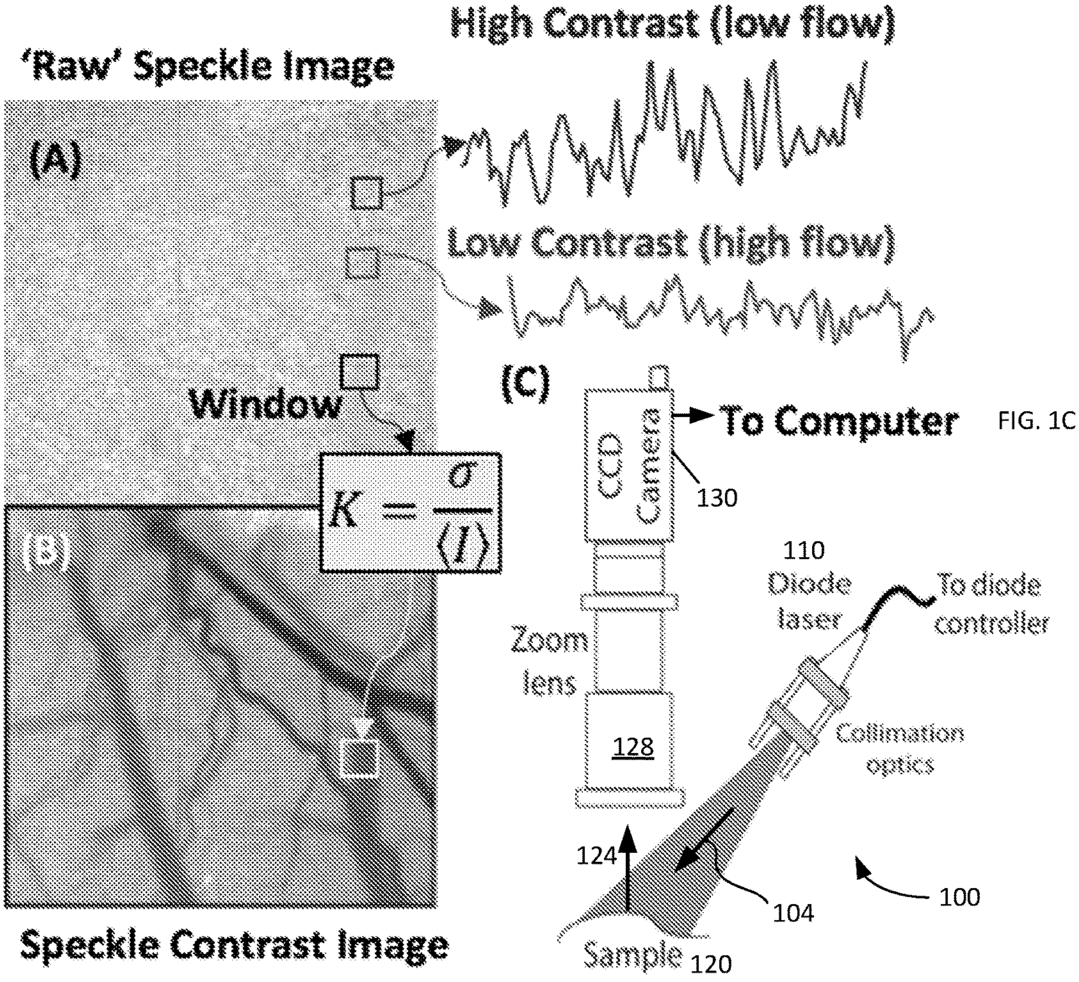
FIGS. 1A, 1B, and 1C provide illustrations to the Laser Speckle Contrast Imaging (LSCI) methodology. Here.

The recently developed and publicized software-based single shot synthetic MESI (syMESI) methodology (see, for example, PCT/US2022/022734) solves the problems associated with the multi-exposure-time time-averaging MESI-based implementation of the LSCI by simultaneously avoiding the need to control power of laser light irradiating the target scene (and thus allowing the user to revert to the practical use of the basic, simpler LSCI system schematically depicted in, for example, FIG. 1) and, at the same time, providing the quantitative assessment of the particle movements in the target that the conventional, single-exposure-time LSCI approach is not capable of providing. Thus, syMESI allows one to emulate the same result as those achieved with MESI but with the use of a traditional LSCI apparatus and using only one, single exposure. A typical hardware/software arrangement for syMESI was discussed in reference to FIGS. 5A, 5B, 5C of PCT/US2022/022734 and for that reason will not be addressed here in any detail. As discussed in PCT/US2022/022734, data representing raw speckle images that would be—under the conventional MESI regime recorded at longer exposure time do not have to be empirically recorded by, instead, can be synthesized or generated numerically by spatially averaging raw speckle image(s) that has/have been recorded practically at a shorter exposure. (The experimentally recorded raw speckle image is that acquired directly with/read-on by the optical detector, in a snap shot and not yet modified after such acquisition). For example, speckle images at 1 ms exposure duration can be synthesized by spatially averaging 4 pixels of a 0.25 ms speckle image. In one example, the averaging can be accomplished with a 2×2 moving window or by 2×2 binning. At each exposure duration—whether the one at which the speckle image has been acquired empirically or the one at which the speckle image has been synthesized numerically, speckle contrast is then computed with the use of a temporal, spatial, or spatio-temporal speckle image processing scheme. Synthetic speckle contrast for corresponding synthetic exposure time fit to the traditional MESI equation for estimation of flow. Both the MESI methodology and the syMESI methodology provide for quantitative imaging of an absolute value (as opposed to relative value determined with respect to some reference value) or a baseline of flow and increased the dynamic range of flow detection as compared with the conventional LSCI technique. (Notably, the term "absolute value" is defined herein not in a mathematical sense as a modulus of such value but as a value that represents the intrinsic magnitude of a parameter being measured without comparing it to any other, while the "relative value" of the parameter is determined based on comparison with a reference magnitude of a similar parameter.)

A person of skill will now immediately appreciate that both the traditional hardware-based multi-exposure speckle imaging (MESI) approach and the software-based synthetic multi-exposure (syMESI) approach utilize, for formation of raw speckle image(s), a single category, kind of light—light scattered by the target scene or object, and both require the acquisition of speckle images/image at short exposure duration (50 μs to 80 ms for MESI/(50 μs for syMESI). Acquisition of images at short exposure time is, as is well recognized, a non-trivial instrumental challenge. Since speckle contrast is conventionally computed as the variance of intensities normalized to the mean value of intensities, the average intensity of the backscattered light at the camera sensor (optical detector) necessarily has to be large enough to overcome noise of the detector and to utilize the full dynamic range of the detector (for example, 127 a.u. for 8 bit and 32768 a.u. for 16 bit optical camera). This, in turn, leads to a requirement to have the target-illuminating power of light generated by the employed laser source to necessarily be high and/or expensive or, otherwise, high-sensitivity optical cameras/detectors have to be used. (The "high" target illuminating laser power in current context is that which produces local irradiances greater than ANSI approved limits for laser/skin exposure or other conventional limits for laser-tissue exposure.)

This limitation of the need to use the high-power laser sources reduces the significance of MESI/syMESI in clinical applications, as damage due to laser exposure simply does not allow one to work with such high target-illuminating powers, especially for sensitive tissues such intraoperative brain imaging and ophthalmology. Notably, while detection sensitivity can be, of course, increased with the use of SPAD array or EMCCD cameras, such use also increases the overall instrument cost, form factor, and complexity.

Embodiments of the invention obviate the above-described limitations and problems that are inherent in methodologies of related art by devising a speckle imaging system that employs an optical interferometer apparatus (such that light, acquired by the optical imaging portion of the overall speckle imaging system, is a composite of multiple light beams arriving to the optical imaging portion from two different origins and only one of which represents light backscattered by the target object or scene) and new speckle visibility algorithm to implement fast quantitative imaging the motion present at the object or scene while utilizing the optical image transformation according to the teachings of either conventional LSCI method, or MESI method, or syMESI method.

It is understood that implementations of the discussed idea of the invention are directed to non-intrusive imaging of and determining a motion present at various objects—be it an inanimate object or space containing certain moving portions or elements or living objects such as a biological tissue hosting a flow of blood—all of which are within the scope of the invention. That said, the discussion of embodiments of the invention below is presented with the specific non-limiting examples of a target that is a biological tissue, for simplicity and certainty of presentation.

The idea of the invention stems from the realization that the use of the optical interferometer apparatus between the optical illumination system (that includes a source of light such as a laser source of light, in a specific case) and the optical imaging system (that includes an optical detector) under the condition that the target object or scene (that serves as the source of backscattered light for laser speckle being imaged) is located in the sample arm of such interferometer—while the useful light (collected by the optical imaging system at the output of the interferometer apparatus) contains not only the backscattered by the target object but also light propagating through the reference arm of the interferometer—boosts the weak dynamic signal that would be provided by the backscattered light only, by itself. The use of such configuration of the embodiment of the invention was shown to enable the overall speckle imaging system to substantially always operate in such a regime in which the value of speckle variance of the raw speckle image (empirically acquired at the detector in light output from the optical interferometer apparatus) was ascertained or determined with certainty and precision while maintaining this value of speckle variance to be larger than a value of variance of noise of the optical detector substantially regardless of a level of intensity of light illuminating the target object or scene placed in the sample arm of the interferometer apparatus of the speckle imaging system. By increasing the speckle variance to be over the noise level with the use of the embodiment of the invention, the signal to noise ratio of the measurement is advantageously increased. The formation of such operational regime due to the use of the optical interferometer apparatus as part of the overall speckle imaging system provides a clear operational advantage to embodiments of the invention, in stark contradistinction with operation of any speckle imaging system of related art which—as soon as the level of intensity of light illuminating the object/scene falls below a certain level—necessarily and recognizably does not allow for any reliable, repeatable, accurate, and/precise determination of the speckle variance that is dominated by the variance of noise of the optical detector.

Furthermore, as practical implementations of the idea of the invention empirically demonstrated, the temporal resolution of the proposed speckle imaging methodology was limited only by the camera frame rates; and a high frame rate optical camera/detector was not required for the methodology to work. As a result, the proposed methodology can be used to perform quantitative video rate multi-exposure speckle imaging (which is about 10 times faster than current state of the art). The implementation of the idea of the invention provides an additional advantage in that the strength of interferogram collected in light output from the optical interferometer apparatus of the system—and hence the dynamic range of the overall measurement—can be tuned or varied at will by adjusting, for example, the intensity light in the reference arm (with the use of a neutral density filter, in one specific non-limiting case).

Notably, and in stark contradistinction with acquisition of laser speckle under different circumstances such as, for example, in the case when the optical coherence tomography (OCT) system is used, the embodiment of the invention is configured such that the optical interferometer apparatus does not require or even does not allow for a change of optical path difference (OPD that would otherwise be caused by, for example, change of phase differential) between light portions propagating through its sample and reference arms.

Figure 4:
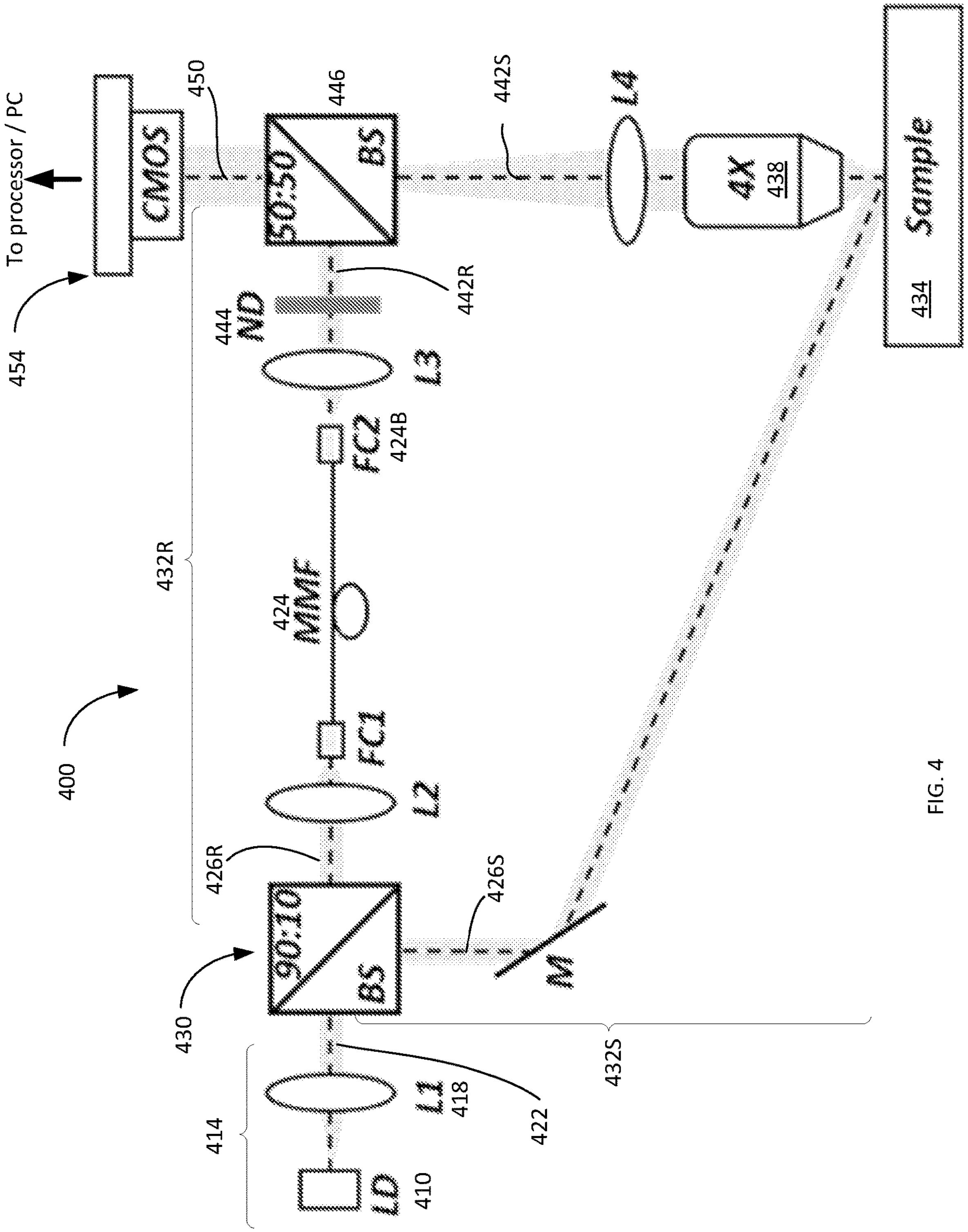
FIG. 4 schematically illustrates a speckle imaging system configured according to the idea of the invention.

A representative embodiment 400 of the speckle imaging system configured according to the idea of the invention is schematically shown in FIG. 4, and, as shown, includes an optical interferometer apparatus which in this specific case is configured as a Mach-Zehnder interferometer (with understanding that in related embodiment the interferometer can be structured differently, for example according to a Michelson configuration, for example).

Light from a light source 410 (which, in one practical implementation was a single mode laser diode, LD, generating linearly polarized CW light at $\lambda$=638 nm and 150 mW) of the optical illumination system 414 was spatially transformed with the use of optics 418 (as shown—collimated with an aspheric lens L1, Thorlabs C171TMD-B, f=6.20 mm, NA=0.30) to produce the input beam 422, which was then split into a sample beam of light 426S and a reference beam of light 426R with the use of a non-polarizing beam splitter 420. Generally, the value of the light-splitting ratio did not affect the principle of operation of the embodiment. In the illustrated case, however, the Thorlabs BS076 model of the beamsplitter 430 was used such that about 10% of the input optical power of the beam 422 was coupled as reference light 422A into the reference arm 432R of the interferometer (here, shown to contain an step-Index multimode fiber optic patch cable 424, Thorlabs M124L01, diameter Ø400 μm, 0.50 NA), while about 90% of light power of the beam 422 was delivered in the sample arm 432S as the sample light 422S to substantially spatially uniformly illuminate the target sample 434.

The specific geometry of illuminating the sample with the sample light 426S was proven to not affect the operation of the embodiment, but in the illustrated case such illumination was provided at an angle of about 30 to 45 degrees with respect to the normal drawn with respect to the surface of the sample 434. Similarly, the specific contents of the reference arm 432R of the interferometer apparatus were proven to not affect the operation of the embodiment 400 (a related embodiment may be implemented, for example, without the use of the optical fiber cable 424. In the specific example of FIG. 4, reference light at the output of the multimode fiber 424 was collimated by a fiber collimator FC2, 424B (Thorlabs F230FC-780-780 nm, f=4.51 mm, NA=0.55). Optionally, in at least one of the sample and reference arms 432S, 432S a device configured to control intensity of light propagating through such arm can be used—as shown in the example of FIG. 4, such device was configured as a spatially-repositionable neutral density filter ND, 444.

The sample light 426S, that interacted with and was backscattered by the sample 434, was collected by a lens 438 (shown here as an optical objective, 4×, NA=0.10, Olympus). Light 442S of the collected backscattered at the sample beam 426S and light 442R of the reference beam 426R at the output end of the reference arm 432R were then spatially overlapped/combined with another beam splitter 446 (here—a 50/50 beam splitter from Thorlabs; CCM1-BS013) to from light 450 at the output of the optical interferometer apparatus and imaged with the optical imaging system 454 of the embodiment 400 that included, in one specific case, by a CMOS camera (Basler acA2000-165umNIR). In one implementation, the operation of the speckle imaging system was devoid of changing an operational parameter of the optical interferometer apparatus (with an optional exception of varying the intensity of reference light 442R). In one implementation, the raw speckle images were continuously recorded at a 100 Hz frame rate and 100 μs exposure time.

The embodiment 400 was equipped with a computer processor (or computer system, or data processing electronic circuitry; not shown in FIG. 4) configured at least to transform images acquired at the optical detector of the optical imaging system 454 and, at least optionally, to govern the operation of the optical illumination system 414 and/or light intensity controlling device (such as device 444, when present). Such computer processor, operably connected with the optical imaging system 454 to receive electrical signal(s) from the system 454, was complemented with a computer-readable tangible non-transitory medium carrying a computer-readable program code. The code contained instructions to the processor to at least determine and/or display a speckle contrast characteristic (such as, for example, speckle variance and/or of a raw speckle image acquired with the system 454 in the light output 450 from the optical interferometer apparatus), and, optionally, to perform additional optical-image transformation steps such as, for example, determining a speckle contrast characteristic of the empirically acquired raw speckle image as a function of a ratio of intensity of the reference light 442R to intensity of the light 450 at the output of the interferometer apparatus (as will be discussed in more detail below). Instructions, provided to the processor by the code contained on the storage medium associated with the computer processor, are in one case configured to enable calculation of speckle contrast characteristic in either temporal domain, or a spatial domain, or a spatio-temporal domain, and/or with the use of a traditional MESI or syMESI algorithms. For example, in one embodiment, the instructions provided to the processor are configured to cause the processor to calculate a value of speckle contrast of the raw speckle image acquired in light 450 for each identified pixel (or group of pixels) of the optical detector of the system 454 either as a ratio of a normalized value of a standard deviation of intensities of light at pixels within a chosen area of the optical detector surrounding such identified pixel to a mean value of such intensities, or as a ratio of a normalized value of a standard deviation of intensities of light at the identified pixel to a mean value of said intensities of light at the identified pixel calculated over multiple exposure times.

A skilled artisan having the advantage of the above discussion can readily appreciate that the effect of the use of the proposed embodiment of the invention is to ensure the operation of the system in a regime in which the useful and/or informative signal (that is, that representing the backscattered by the sample light always overcomes the noise of optical detector) at low exposure durations (typically or about 100 μs) and thereby to enable a quantitative determination of an absolute value (and not the relative value; absolute measurement) and/or imaging of a motion at the sample (for example, in case of a biological tissue—that of a blood flow). The use of the optical interferometer apparatus increases the measured signal (by boosting power of the reference arm), while holding noise relatively constant, thereby allowing for the signal-to-noise ratio to be higher than conventionally possible in situations with small signal and a large noise background.

For laser speckle imaging performed with the use of the embodiment 400, for example the electric field of light 450 at the output of the optical interferometer apparatus can be expressed as $$E(t)=E_{sample}(t)+E_{reference}(t) \tag{1}$$

Here, $E_{sample}$ (t) is the electric field of light 442S backscattered from sample and $E_{reference}$(t) electric field of the reference light 442R. The intensity of light 450 received and detected by the optical detector of the optical imaging system 454 is:

$$I(t)=|E(t)|^2 \tag{2}$$

$$I(t)=\left|E_{sample}(t)\,E^*_{sample}(t)\right|+\left|E_{reference}(t)\,E^*_{reference}(t)\right|+2\mathbb{R}\mathbb{E}\left|E_{sample}(t)\,E^*_{reference}(t)\right| \tag{3}$$

Following Sigert relation discussed by, for example, R. Bandyopadhyay et al. (in "Speckle-visibility spectroscopy: A tool to study time-varying dynamics," Rev. Sci. Instrum. 76, 1-11, 2005), the autocorrelation of the measured intensity can now be expressed as:

$$g_2(\tau)=1+\beta\left[\frac{\langle I_s(t)\rangle^2}{(\langle I_s(t)\rangle\langle I_r(t)\rangle)^2}|g_1(\tau)|^2+\frac{2\langle I_s(t)\rangle\langle I_r(t)\rangle}{(\langle I_s(t)\rangle+\langle I_r(t)\rangle)^2}g_1(\tau)\right] \tag{4}$$

$$g_2(\tau)=1+\beta_1\,|\,g_1(\tau)\,|^2+\beta_2 g_1(\tau) \tag{5}$$

Here, $$\beta_1=\beta\left(1-\frac{I_r(t)}{I_T(t)}\right)^2,\ \beta_2=2\beta\frac{I_r(t)}{I_T(t)}\left(1-\frac{I_r(t)}{I_T(t)}\right),$$

$I_T=I_s+I_r$. Following the teachings of R. Bandyopadhyay et al., one can express speckle visibility as, $$V_2(t)=\beta_1\int_0^T 2\left(1-\frac{t}{T}\right)|g_1(t)|^2\frac{dt}{T}+\beta_2\int_0^T 2\left(1-\frac{t}{T}\right)|g_1(t)|\,\frac{dt}{T} \tag{6}$$

Assuming Lorentzian distribution, $g_1(t)=e^{-t/\pi c}$, the speckle contrast is then expressed as:

$$K=\left[\beta_1\frac{e^{-2x}-1+2x}{2x^2}+2\beta_2\frac{e^{-x}-1+x}{x^2}\right]^{1/2} \tag{7}$$

$$K=\left[\beta\left(1-\left(\frac{I_r(t)}{I_T(t)}\right)^2\right)\frac{e^{-2x}-1+2x}{2x^2}+4\beta\frac{I_r(t)}{I_T(t)}\left(1-\frac{I_r(t)}{I_T(t)}\right)\frac{e^{-x}-1+x}{x^2}\right]^{1/2} \tag{8}$$

Accordingly, in an embodiment of the invention, a speckle contrast characteristic of the acquired raw speckle image is determined as a function of a (time-dependent) ratio of intensity of the reference light 442R to intensity of the overall output light 450. This Eq. 8 representing a speckle visibility obtained with the use of the embodiment 400 of the system of the invention can be further fit by performing hardware based multi-exposure (MESI) or software based synthetic multi-exposure (syMESI) data processing.

Figure 5:
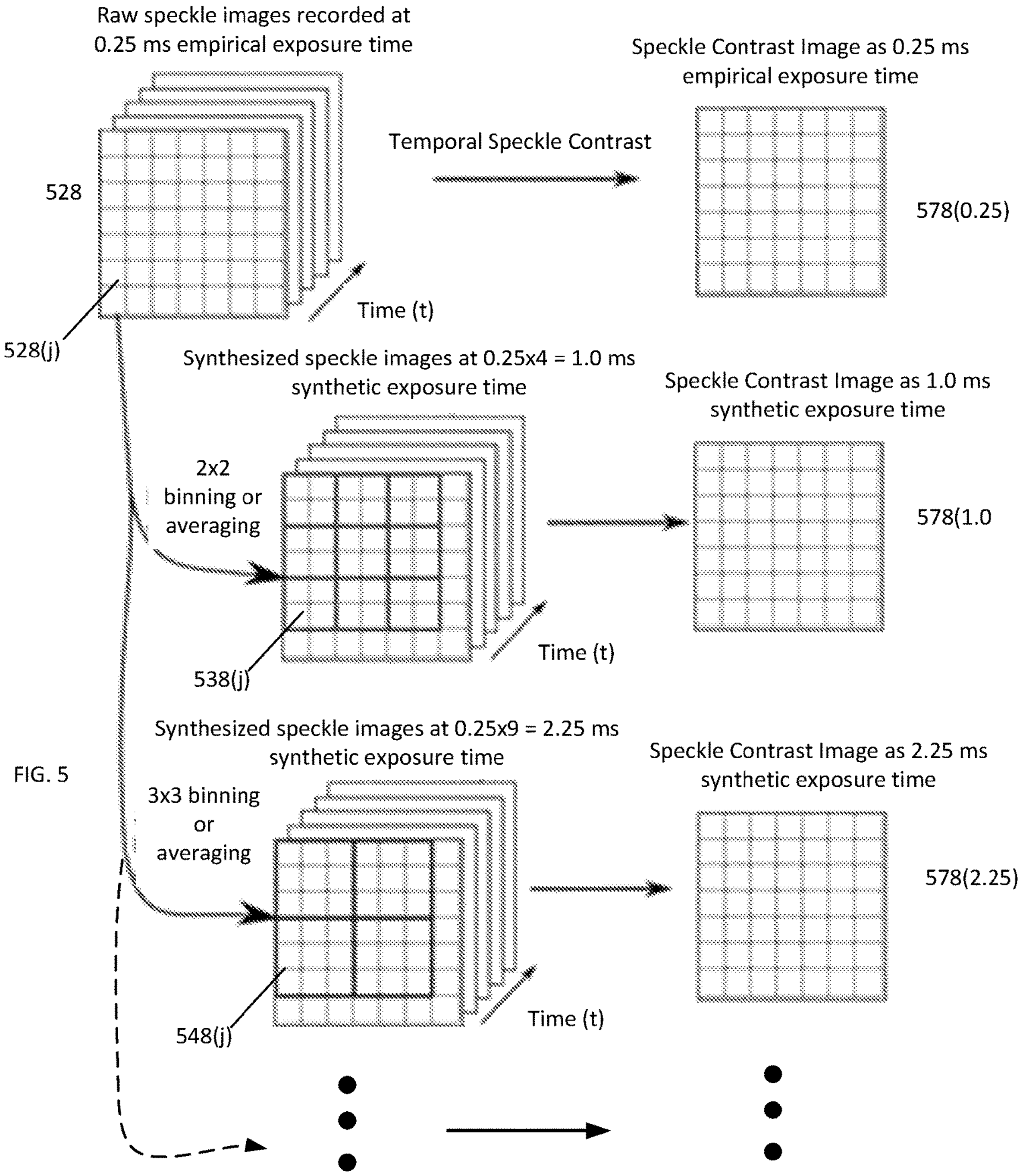
FIG. 5: The use of synthetic Multi-Exposure Speckle Imaging methodology while collecting optical data with the embodiment of FIG. 4. Raw speckle images at longer exposure can be synthesized by spatially averaging images at shorter exposure. For example, speckle images at 1 ms exposure duration are synthesized by spatially averaging 4 pixels of a 0.25 ms speckle image. The averaging can be accomplished with a 2×2 moving window or by 2×2 binning. At each exposure duration, speckle contrast is computed at each image pixel in the temporal domain, by calculating the ratio of the standard deviation to mean of intensities.

Consider, for example, the implementation of the speckle imaging with the use of system 400 and the syMESI approach and algorithm discussed in reference to FIG. 4 of PCT/US2022/022734, which is reproduced here as FIG. 5. Here, at least one or a series of multiple raw speckle images 528 may be acquired by the optical detector at an only, single, fixed exposure time (empirical acquisition of raw speckle data; here—at 0.25 ms), using the embodiment 400 of the speckle imaging system (in which the system 400 necessarily does not include an apparatus that is configured to maintain a power of the light output 450 to be substantially constant over exposure time). Either one, chosen or—alternatively—each of these raw speckle images is then modified/transformed/converted to corresponding synthetic multi-exposure-time images (that is, images corresponding to multiple synthetic exposure times) by spatially averaging the camera recorded chosen image 528(*j*) with an appropriate spatial window or aperture (interchangeably—binning aperture). The shape of the aperture is preferably polygonal (considering the pixelated nature of raw speckle images 528) and, in a specific case, the averaging spatial aperture may have a shape of a concave polygon—that is, a polygon at least one angle of which exceeds 180 degrees. Here, as shown in the example of FIG. 5, spatially averaging the chosen raw speckle image 528(*j*) taken at an empirical exposure time of 0.25 ms with a 2×2 square window/binning aperture yields a modified image that is a synthetic exposure image 538(*j*). This image 538(*j*) is a speckle image of the scene 120 corresponding to a synthetic (not empirical) exposure time of 1 ms. Each pixel of the synthetic 1 ms image 538(*j*) is an average of 2×2=4 adjacent pixels of the camera-acquired 0.25 ms empirical exposure time image 528(*j*). In this manner, FIG. 5 also illustrates how a modified speckle image 548(*j*) corresponding to a synthetic exposure time of 2.25 ms can be formed. By repeating this process multiple times—as indicated in FIG. 5 with ellipses—with variously-shaped and/or sized binning windows for at least one (and, if needed, more than one) empirically recorded raw speckle image from the set 528, the user or the system produce a plurality of modified speckle images each of which represents a speckle image of the scene corresponding to a corresponding synthetic exposure time (of a plurality of decided upon synthetic exposure times).

Additionally and optionally—and referring again to FIG. 5—in at least one specific embodiment of the invention, the information about the motion present at the imaged sample/object/scene 434 (for a non-limiting example—information about blood flow in the biological tissue) may at least in one case be quantified by determining the temporal speckle contrast at each image pixel for all synthetic exposure times, i.e., by computing the value of K at each pixel according to Eq. 8. Thereby, the set(s) of modified speckle images 538(*j*), 548(*j*), and so on is transformed to a respectively-corresponding images containing information about speckle contrast. See the speckle contrast image 578(0.25) representing the spatial distribution of speckle contrast within bounds of the empirically-acquired at the exposure time of 0.25 ms image(s) 528. See also the speckle contrast image 578(1.0) representing the spatial distribution of speckle contrast within bounds of the generated, by spatial binning average, synthetic image(s) 538(*j*) corresponding to synthetic exposure time of 1.0 ms. See also the speckle contrast image 578(2.25) representing the spatial distribution of speckle contrast within bounds of the generated, by spatial binning average, synthetic image(s) 448(*j*) corresponding to synthetic exposure time of 2.25 ms. Furthermore, at each pixel of such speckle contrast image(s) one can thus assess the speckle visibility (expressed in at least one example as a plot or curve of speckle variance vs synthetic exposure time, e.g., FIG. 2) that can further be fit to either a single-scattering quantitative speckle contrast spectroscopy model (see Parthasarathy, A. B., et al., in *Optics Express* 16, 1975-1989; 2008)) or a diffuse-scattering quantitative speckle contrast spectroscopy model (see Valdes, C. P. et al. in Biomedical optics express 5, 2769, doi: 10.1364/BOE.5.002769 (2014).) to estimate an index of motion at a portion of the interrogated scene 434 represented by a given pixel of the chosen raw speckle image (and, in the case when the scene is a biological tissue—an index of blood flow at the corresponding portion of the tissue).

Notably, the spatial averaging can be performed using a variety of approaches as befitting the application—including pixel-wise binning (expressly depicted in FIG. 5) with spatial windows or apertures of various sizes and/or shapes placed substantially in the same location of the chosen raw speckle image, or with a spatial window or aperture of a fixed size and/or shaped that is repositioned across the chosen raw speckle image. The latter can retain the high spatial resolution of the images. These operations can be performed using standard image processing algorithms. Furthermore, as the skilled artisan has already appreciated from the discussion above, the spatial averaging is not restricted to a rectangularly-shaped spatial window or binning aperture. For example, with reference to FIG. 5, a 3×2 spatial window can be used to synthesize 0.25×6=1.5 ms exposure image. As applications require, windows of arbitrary (optionally-polygonal) shapes and sizes can be used.

Discussion of Experimental Results

As was already alluded to above, one of practical advantages provided by the use of the embodiment of the speckle imaging system incorporation the optical interferometer apparatus characterized by the substantially unchangeable OPD between the sample and reference arms is the ability of such system to obtain/to boost weak dynamic signal, especially on the background of the ever-present noise of the optical detector. The use of embodiment 400 provided experimental validation of this advantage and demonstrated that imaging and quantification of absolute numerical parameter of a motion present at the target object could be carried out substantially regardless of how low the intensity of sample-illuminating light 426S was. To this end, synthetic MESI images and speckle visibility curves were computed (according to the algorithm referenced above with respect to FIG. 5) for additional multiple exposures varying from 100 μs to 10 ms starting with a raw speckle image(s) acquired at a single exposure time. The raw speckle image(s) were collected from tissue simulating flow phantom—while flowing 20% intralipid through a 200 μm×150 μm flow channel, at flow rates 1 to 7 mm/s.

Figure 6:
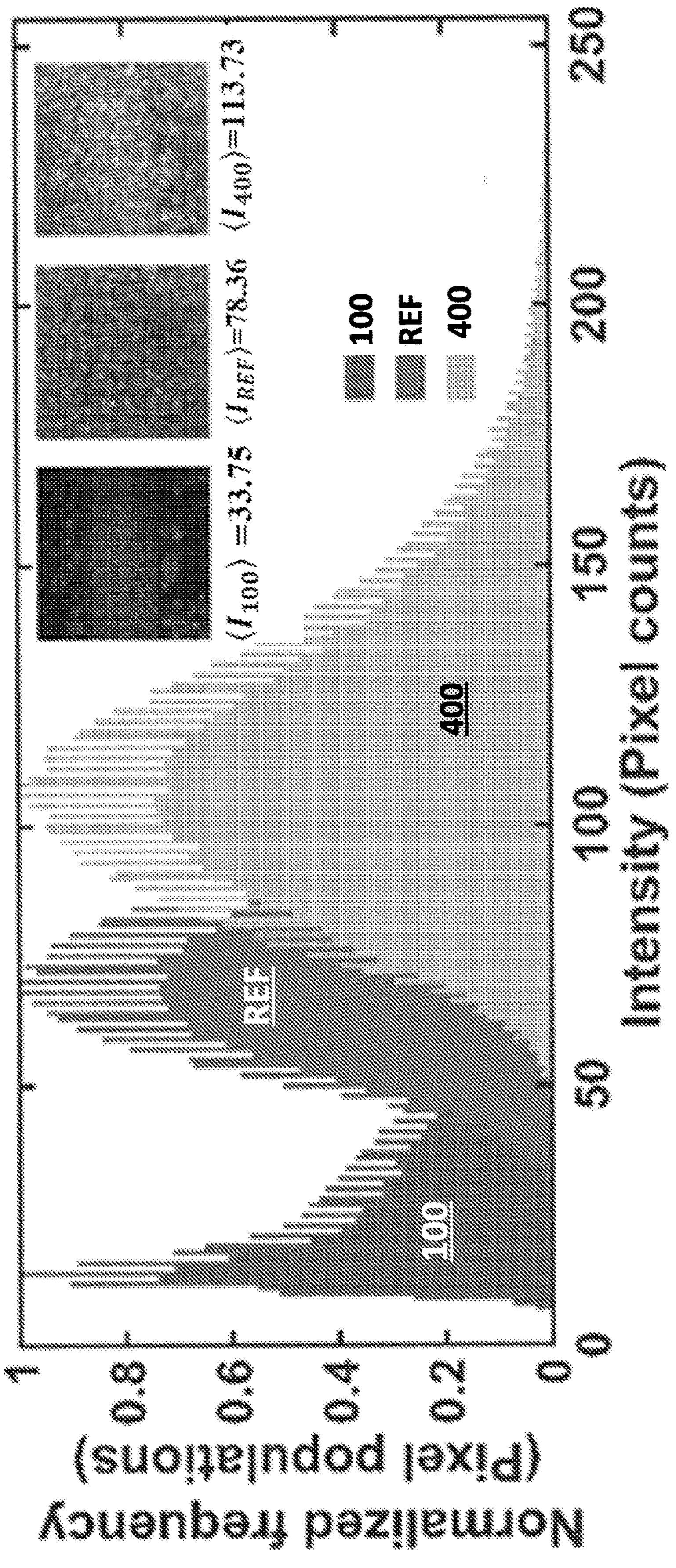
FIG. 6: Characterization and comparison of results of synthetic multi-exposure speckle imaging performed with the system 300 of related art (see FIG. 3) and that configured according to the idea of the invention (see system 400 of FIG. 4). Histograms of pixel intensities for these two measurements, with intensity maps of the corresponding raw speckle images shown in insets.

The results presented in FIG. 6 attest to the fact that the system 400 necessarily operates in a regime in which the weak dynamic signal representing light 442S is boosted to overcome the noise of the optical detector. Here, FIG. 6 compares intensity histograms of the raw speckle images acquired with the system 100 of FIG. 1 and the system 400 of FIG. 4. In case of the utilizing the embodiment 100, the average intensity of light at the optical detector of the imaging camera was 33.75 (a.u.), which is 4 times lower than the intensity required to fill the dynamic range of the 8 bit camera sensor. Also, due to the low photon counts, imaged speckle is underdeveloped. See histogram 100 and inset $\langle I_{100} \rangle$. Next, only the reference light propagating through the reference arm was introduced, embodiment 400, with an average intensity of 78.36 (a.u.). As multimode fiber was employed in the reference arm, one can control/vary/modify the intensity of the reference light to ensure that that resulting speckle pattern does not saturate the optical detector (sensor of the optical imaging system or camera). See histogram REF and inset $\langle I_{REF} \rangle$. Finally, when judiciously overlapping the backscattered by the sample light 442S with the reference light 442R and interfering those at the optical detector, the overall average intensity was increased to 113.73 (a.u.). See histogram 400 and inset $\langle I_{400} \rangle$ From the inset we can clearly see dynamic speckle from the flow region boosted by the reference arm due to the heterodyne scheme compared to homodyne scheme. Further, the use of the embodiment of the invention proved the ability of the speckle imaging process to ensure quantitative imaging and determination of an absolute characteristic of the motions in presence of the noise at the optical detector.

FIGS. 7A, 7B demonstrates the reconstruction of quantitative speckle contrast images with the embodiment of the invention (FIG. 7B) and comparison of the results with those produced by the use of the traditional speckle imaging (embodiment 100; with low photon counts typical of short exposure time <1 ms). FIG. 7A illustrates that the average intensity detected by the optical detector of the embodiment 100 was low and the image was dominated by the noise of the optical detector. Application of MESI/syMESI data processing of raw images acquired with the conventional embodiment 100 may yield artificially high speckle contrast values. The resultant image of motion at the object (in this case—the image of blood flow in a biological tissue) had poor sensitivity flow in the channel present in the middle of the image, with the entire image of FIG. 7A resembling that of a static speckle pattern. The use of the embodiment 400, however, overcame this issue by boosting the low mean intensity of light backscattered by sample via interference of this backscattered light with light propagating through the reference arm, and allowed to accurately evaluate speckle contrast image at comparably short exposure time(s). It is evident from several images of FIG. 7B that speckle contrast at exposure time 100 μs for example was incomparably higher than that of FIG. 7B, while at the same time enabling the accurate measurement of the absolute value of the speckle contrast despite the presence of the noise of the optical detector.

Figure 8B:
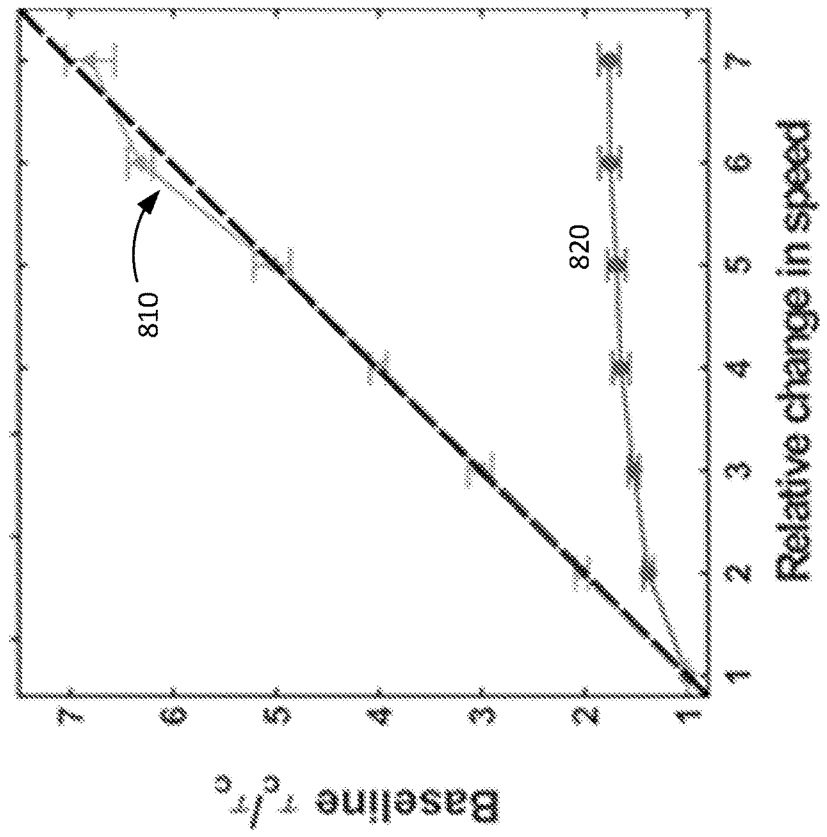
FIG. 8B: Performance of a MESI model with the use of the conventional embodiment 100 of FIG. 1 (curve 820) and the syMESI model with the use of the embodiment 400 of FIG. 4 (curve 810). In determining the relative changes in motion at the object. Baseline speed: 1 mm/sec. Plot of relative $\tau_c$ to relative speed. Plot should ideally be a straight line (shown as a dashed line). The embodiment of the present invention estimates clearly enhance/extend linear range of relative $\tau_c$ estimates as compared with the use of the conventional embodiment of FIG. 3 or conventional embodiment of FIG. 1. Error bars indicate standard error in relative correlation time estimates. Measurements were performed using microfluidic phantom with no static scattering layer Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.
Figure 8A:
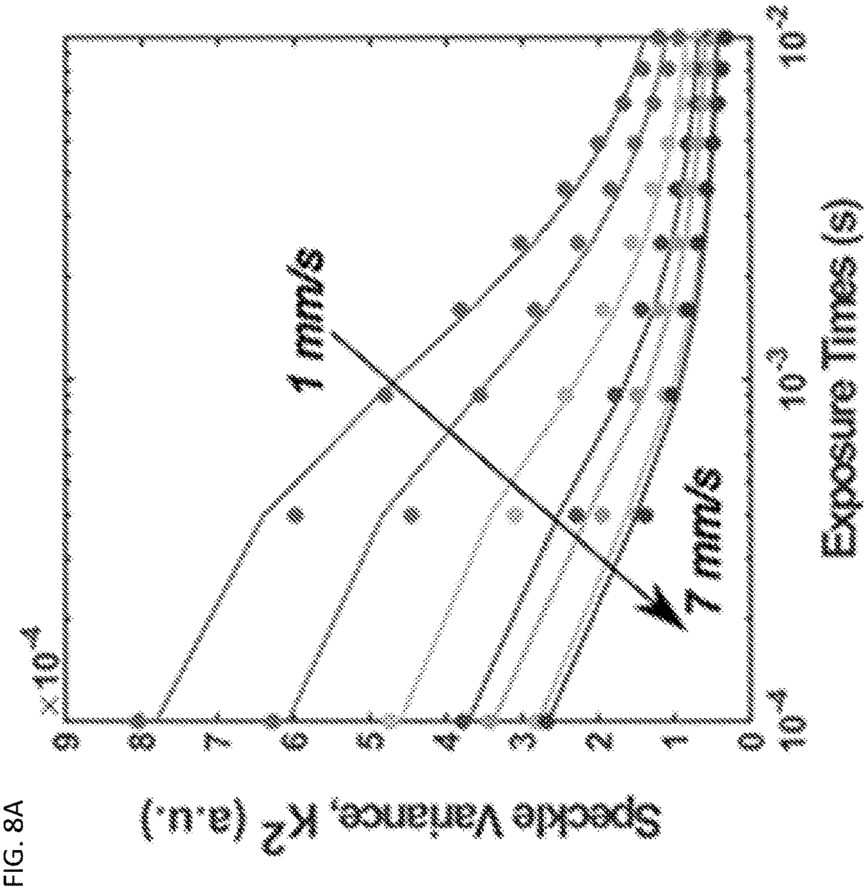
FIG. 8A shows the fit of the synthetic MESI data obtained with the use of the embodiment 400 of FIG. 4 to the speckle model: Speckle variance as a function of synthetic exposure duration for different speeds. Measurements were made on samples with no static scattering layer.

Moreover, the use of the embodiment 400 demonstrated linearity of large changes of the motion at the sample (for example, large changes in blood flow of the biological tissue) in presence of the optical detector noise in contradistinction with results obtained with the use of the conventional embodiment 100; see FIGS. 8A, 8B.

Here, the experimental setup 400 (FIG. 4) was used in conjunction with the synthetic exposure technique to perform controlled experiments on the microfluidic samples. Intralipid 20% was pumped through the sample using the syringe pump at different speeds ranging from 1 mm/sec to 7 mm/sec in 1 mm/sec increments. One hundred (100) raw speckle images were captured for each flow rate at 100 μs exposure duration. Using synthetic multi-exposure algorithm average heterodyne speckle contrast, as a function of exposure time, were calculated for the flow region. The so procured synthetic multi-exposure speckle contrast data were then fit to Eq. 8, by holding β and $$\frac{I_r(t)}{I_T(t)}$$

constant. FIG. 8A clearly shows that the model fits the experimental data very well. The correlation time (a quantitative metric of the motion, blood flow) was estimated by having $\tau_c$ as a fitting parameter. Next, the proof was sought of whether the $\tau_c$ estimates obtained using the speckle imaging instrument 400 were more accurate than those obtained with traditional single exposure LSCI measures by comparing the respective estimates of the relative correlation time measures. Correlation time estimates from traditional single exposure measures was obtained using conventional methods, for example using the procedure detailed by D. A. Boas, et al. ("Laser speckle contrast imaging in biomedical optics," J. Biomed. Opt. 15, 011109, 2010). Relative correlation time measures were defined as $$\frac{Baseline\ \tau_c}{\tau_c},$$

Correlation time estimates were obtained from the fits performed in FIG. 8A. The $\tau_c$ estimates obtained with the system 400 were compared with those obtained with traditional single exposure utilizing the conventional system 100 of related art estimates of $\tau_c$ at 100 μs to evaluate the efficacy of predicting relative flows. Ideally, relative correlation measures would be linear with relative speed. Relative correlation times were obtained for a baseline flow of 1 mm/sec.

FIG. 8B shows that the proposed speckle model in conjunction with the use of speckle imaging system 400 and synthetic multi-exposure speckle imaging scheme achieved linearity of relative correlation measures over a large flow range (nearly 6-fold; compare data curve 810 with the linear dashed line) while easily overcoming the presence of the optical detector noise. At the same time, the use of traditional single exposure scheme of embodiment 100 (see curve 820) failed to provide any relative change of the motion at the imaged object/scene since the useful (backscattered by the object) signal was completely buried by the noise of the optical detector. Indeed, to evaluate linearity of relative change of motion (blood flow in one specific example), the average detected intensity needed to be at least 127 (a.u) for a 8 bit optical detector and 32768 (a.u) for a 16 bit optical detector. This allowed full utilization of the dynamic range of the optical imaging system and full development of the speckle. The use of embodiment 100, on the other hand, at such short exposure time (<1 ms) fell short of achieving this dynamic range in each case when and unless high laser power and sensitive detector were used.

The skilled artisan will now appreciate practical advantages provided by the use of the proposed embodiment of the speckle imaging system over comparable optical instruments of related art in imaging/measuring a motion occurring at the target object or sample or scene:

the proposed instrument requires only addition of a reference arm to the conventional speckle imaging apparatus—this can be achieved in free-space as shown in FIG. 4, or with the use of an optical fiber component, or other similar arrangement. Any low power laser source and low-cost camera (as low as 1 megapixels, low bit depths and light sensitivities) can be used.

No special expensive high-power laser or instruments are required for overcoming the optical detector noise.

In the case of utilizing single-shot imaging, the temporal resolution of the approach is limited only by the frame rate of the optical detector; a high frame-rate camera is not required for the methodology to work. As a result, the discussed embodiment can be used to perform quantitative video rate multi-exposure speckle imaging (about 10 times faster than current state of the art).

The strength of the acquired interferogram, and hence the dynamic range of the measurement, can be easily by adjusting the intensity of light in the reference arm.

Embodiments of the invention can be readily used in a wide variety of applications. For example, it can be applied in those applications that utilize laser speckle contrast imaging for blood flow imaging (including, but not limited to imaging of skin microvascular function and dysfunction, wound healing angiogenesis, diagnosis of tissue burns, skin cancer, endoscopic surgical procedures and GI tract surgery, ulcer and/or cardiovascular studies, ophthalmology, diabetes, cerebrovascular studies and especially, intraoperative surgery. It can be also advantageously utilized in quantification of speckle fluctuation dynamics in any multi-speckle detection system, including that applied for diffuse speckle contrast analysis, laser speckle rheology and speckle-based thrombosis measurements.

Contents of each of related art references and/or articles identified in this disclosure is incorporated herein by reference.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The term "image" generally refers to an ordered representation of detector output corresponding to spatial positions. For example, a visual image may be formed, in response to a pattern of light detected by an optical detector, on a display device X such as a video screen or printer. The term "quantitative" is defined as that which is or may be represented by quantity.

The invention as recited in claims appended to this disclosure is intended to be assessed in light of the disclosure as a whole, including features disclosed in related art to which reference is made.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A speckle imaging system comprising:

an optical illumination system of the speckle imaging system including a source of light and configured to produce a light output at an output end of the optical illumination system, wherein the speckle imaging system is configured to detect a motion at a scene;

an optical interferometer apparatus of the speckle imaging system, the optical interferometer apparatus having a reference arm and a sample arm and optically coupled with the output end of the optical illumination system to receive light of the light output from the output end of the optical illumination system, an optical imaging system of the speckle imaging system, the optical imaging system containing an optical detector system that is optically coupled with an output end of the optical interferometer apparatus to receive the light of the light output through the optical interferometer apparatus;

a computer system, operably connected with the optical imaging system and configured to receive an electrical signal therefrom, wherein the electrical signal represents a raw speckle image formed at the optical detector system in light output from the optical interferometer apparatus, wherein the light output includes sample light, that has interacted with a target sample in the sample arm and that contains a speckle pattern representing the target sample, and reference light;

and a computer-readable tangible non-transitory medium comprising a computer-readable program code on which are stored computer-readable instructions such that, when the instructions are executed by a processor of the computer system, the instructions cause the processor at least to determine and/or display a speckle contrast characteristic of said raw speckle image, wherein the speckle imaging system is configured such that an optical phase difference between the sample light propagating through the sample arm and the reference light propagating through the reference arm during acquisition of the raw speckle image remains substantially unchanged.

2. A speckle imaging system according to claim 1, wherein the instructions further cause the processor:

to display said speckle image in a form of a visually perceivable spatial distribution of optical irradiance; and/or to determine and/or display a speckle visibility curve of time-dependent values of the speckle contrast characteristic of said speckle image for target sample exposure times; and/or to determine and/or display a multiplicity of speckle contrast images and/or the speckle visibility curve as a map showing a spatial distribution and/or a temporal distribution of changes of said motion at the target sample.

3. A speckle imaging system according to claim 1, which satisfies at least one of the following conditions:

the speckle imaging system is configured to have a dynamic range of measurement of the speckle contrast characteristic to be dependent on intensity of the reference light; and/or the speckle imaging system includes at least one device configured to control an intensity of the sample light and/or an intensity of the reference light; and/or wherein the instructions further cause the processor to ascertain the speckle variance of said raw speckle image while maintaining such variance to be larger than a variance of noise of the optical detector; and/or wherein the instructions further cause the processor to ascertain the speckle variance of said raw speckle image while maintaining such speckle variance to be substantially larger than a variance of noise of the optical detector regardless of a level of non-zero intensity of a first portion of said light; and/or wherein the instructions further cause the processor to quantitatively determine an absolute value of an index of motion over a portion of the scene or over the entire scene represented by a given pixel of the raw speckle image; and/or wherein the instructions further cause the processor (i) to calculate a value of speckle contrast of said raw speckle image for each identified pixel or group of pixels of the optical detector:

as a first ratio of a normalized value of a standard deviation of intensities of light received from the optical interferometer apparatus at the pixels within a chosen area of the optical detector surrounding such identified pixel to a mean value of said intensities, or as a second ratio of a normalized value of a standard deviation of intensities of light at the identified pixel to a mean value of said intensities of light at the identified pixel calculated over multiple exposure times, and/or (ii) to determine the first ratio and/or the second ratio in a temporal domain, a spatial domain, or a spatio-temporal domain.

4. A speckle imaging system according to claim 1, wherein the instructions further cause the processor to acquire, at only one fixed first empirical exposure time, one or more raw speckle images formed in said light by the imaging system; and to spatially average a chosen raw speckle image of said one or more raw speckle images with use of multiple binning apertures that have spatially different dimensions to form respectively-corresponding modified speckle images, wherein each of said modified speckle images represents a speckle image corresponding to a respectively-corresponding second synthetic exposure time from a plurality of second synthetic exposure times, wherein each second synthetic exposure time from the plurality of second synthetic exposure times is different from one another and from the first empirical exposure time.

5. A speckle imaging system according to claim 4, wherein the instructions further cause the processor to transform each of the modified speckle images into a respectively-corresponding speckle contrast image of a plurality of speckle contrast images and/or speckle visibility curves corresponding to the same chosen raw speckle image.

6. A speckle imaging system according to claim 4, wherein the instructions are configured to further cause the processor to assess, based at least on a speckle visibility curve, a quantitative value of a motion at a portion of a scene irradiated with said light output in operation of the speckle imaging system and represented by said one or more raw speckle images.

7. A speckle imaging system according to claim 4, wherein the instructions are configured to further cause the processor to generate a visually perceivable image of a portion of a scene irradiated with said light output in operation of the speckle imaging system and represented by said one or more raw speckle images, wherein said visually perceivable image displays a spatial distribution of optical irradiance or a quantitative value of a motion at said portion of the scene.

8. A speckle imaging system according to claim 4, wherein the optical imaging system is configured to acquire a sequence of speckle images at only said one fixed first empirical exposure time with time gaps of same or different durations in between immediately neighboring raw speckle images of the sequence.

* * * * *